(12) United States Patent
Appling et al.

(10) Patent No.: US 8,864,754 B2
(45) Date of Patent: Oct. 21, 2014

(54) DEVICE AND METHOD FOR ENDOVASCULAR TREATMENT FOR CAUSING CLOSURE OF A BLOOD VESSEL

(75) Inventors: William M. Appling, Granville, NY (US); Ralph A. Meyer, Argyle, NY (US); Theodore J. Beyer, Queensbury, NY (US); William C. Hamilton, Jr., Queensbury, NY (US); Joe D. Brown, Panama City Beach, FL (US)

(73) Assignee: AngioDynamics, Inc., Latham, NY (US)

(*) Notice: Subject to any disclaimer, the term of this patent is extended or adjusted under 35 U.S.C. 154(b) by 1570 days.

(21) Appl. No.: 12/100,309

(22) Filed: Apr. 9, 2008

(65) Prior Publication Data

US 2008/0188843 A1 Aug. 7, 2008

Related U.S. Application Data

(60) Provisional application No. 60/910,743, filed on Apr. 9, 2007, provisional application No. 60/913,767, filed on Apr. 24, 2007, provisional application No. 60/969,345, filed on Aug. 31, 2007.

(51) Int. Cl.
*A61B 18/20* (2006.01)
*A61B 18/24* (2006.01)
*A61B 19/00* (2006.01)
*A61B 18/00* (2006.01)
*A61B 17/22* (2006.01)

(52) U.S. Cl.
CPC ............. *A61B 18/24* (2013.01); *A61B 19/54* (2013.01); *A61B 2018/00101* (2013.01); *A61B 2019/446* (2013.01); *A61B 2019/5425* (2013.01); *A61B 2017/22068* (2013.01)
USPC .......................................................... 606/15

(58) Field of Classification Search
CPC .................... A61B 19/54; A61B 2017/22068; A61B 2018/00101; A61B 2018/00285; A61B 2019/446; A61B 2019/5425; A61B 18/22
USPC ...................... 606/15, 16; 607/92; 385/14–15
See application file for complete search history.

(56) References Cited

U.S. PATENT DOCUMENTS 1,706,161 A 3/1929 Hollnagel
2,699,770 A 1/1955 Fourestier et al.
(Continued)

FOREIGN PATENT DOCUMENTS

EP 0 311 295 12/1989

OTHER PUBLICATIONS

Authors: Urs Utzinger and Rebecca R. Richards-Kortum, Title: Fiber Optic Probes for Biomedical Optical Spectroscopy, Date: Feb. 2001.*

(Continued)

*Primary Examiner* — Gary Jackson
*Assistant Examiner* — Boniface N Nganga
(74) *Attorney, Agent, or Firm* — Kaplan Breyer Schwarz & Ottesen, LLP; Harry K. Ahn

(57) ABSTRACT

An endovascular laser treatment device for causing closure of a blood vessel uses an optical fiber adapted to be inserted into a blood vessel. An inner sleeve is arranged around a distal portion of the optical fiber core such that both distal ends of the inner sleeve and the optical fiber core form an enlarged light emitting face. The enlarged emitting face provides substantially lower power density while providing the same amount of total energy during a treatment session. An outer sleeve arranged around the inner sleeve acts as a spacer to position the light emitting face away from an inner wall of the blood vessel. The enlarged light emitting face and the outer sleeve acting as a spacer reduces the possibility of thermal run-away and device damage, and reduce the possibility of vessel perforations, leading to less bruising, post-operative pain and other clinical complications.

54 Claims, 14 Drawing Sheets

(56) References Cited

U.S. PATENT DOCUMENTS

| | | | |
|---|---|---|---|
| 3,043,910 | A | 7/1962 | Hicks, Jr. |
| 3,051,035 | A | 8/1962 | Root |
| 3,051,166 | A | 8/1962 | Hounanian |
| 3,068,742 | A | 12/1962 | Hicks, Jr. et al. |
| 3,423,581 | A | 1/1969 | Baer |
| 3,455,625 | A | 7/1969 | Brumley et al. |
| 3,572,325 | A | 3/1971 | Balell et al. |
| 3,622,743 | A | 11/1971 | Muncheryan |
| 3,641,332 | A * | 2/1972 | Reick et al. ............ 362/582 |
| 3,643,653 | A | 2/1972 | Takahashi et al. |
| 3,678,741 | A | 7/1972 | Burley |
| 3,704,996 | A | 12/1972 | Borner et al. |
| 3,710,798 | A | 1/1973 | Bredemeier |
| 3,726,272 | A | 4/1973 | Fukami et al. |
| 3,756,688 | A | 9/1973 | Hudson |
| 3,768,146 | A | 10/1973 | Braun |
| 3,780,295 | A | 12/1973 | Kapron |
| 3,790,791 | A | 2/1974 | Anderson |
| 3,796,905 | A | 3/1974 | Tomii et al. |
| 3,808,549 | A | 4/1974 | Maurer |
| 3,832,028 | A | 8/1974 | Kapron |
| 3,834,391 | A | 9/1974 | Block |
| 3,834,803 | A | 9/1974 | Tsukada |
| 3,843,865 | A | 10/1974 | Nath |
| 3,846,010 | A | 11/1974 | Love |
| 3,849,947 | A | 11/1974 | Bunkoczy |
| 3,858,577 | A | 1/1975 | Bass et al. |
| 3,861,781 | A | 1/1975 | Hasegawa et al. |
| 3,866,599 | A | 2/1975 | Johnson |
| 3,874,783 | A | 4/1975 | Cole |
| 3,880,452 | A | 4/1975 | Fields |
| 3,906,221 | A | 9/1975 | Mercier |
| 3,910,677 | A | 10/1975 | Becker et al. |
| 3,920,980 | A | 11/1975 | Nath |
| 3,932,184 | A | 1/1976 | Cohen et al. |
| 3,972,585 | A | 8/1976 | Dalgleish et al. |
| 4,005,522 | A | 2/1977 | Dalgleish et al. |
| 4,008,948 | A | 2/1977 | Dalgleish et al. |
| 4,087,158 | A | 5/1978 | Lewis et al. |
| 4,148,554 | A | 4/1979 | Magnusson et al. |
| 4,191,446 | A | 3/1980 | Arditty et al. |
| 4,233,493 | A | 11/1980 | Nath |
| 4,273,109 | A * | 6/1981 | Enderby ............ 600/175 |
| 4,380,365 | A | 4/1983 | Gross |
| 4,449,535 | A | 5/1984 | Renault |
| 4,573,761 | A | 3/1986 | McLachlan et al. |
| 4,592,353 | A | 6/1986 | Daikuzono |
| 4,654,532 | A | 3/1987 | Hirschfeld |
| 4,660,925 | A | 4/1987 | McCaughan, Jr. |
| 4,662,368 | A | 5/1987 | Hussein et al. |
| 4,671,273 | A | 6/1987 | Lindsey |
| 4,693,244 | A | 9/1987 | Daikuzono |
| 4,693,556 | A | 9/1987 | McCaughan, Jr. |
| 4,695,697 | A | 9/1987 | Kosa |
| 4,707,134 | A | 11/1987 | McLachlan et al. |
| 4,736,743 | A | 4/1988 | Daikuzono |
| 4,740,047 | A | 4/1988 | Abe et al. |
| 4,743,084 | A | 5/1988 | Manning |
| 4,773,413 | A * | 9/1988 | Hussein et al. ............ 606/7 |
| 4,812,003 | A | 3/1989 | Dambach et al. |
| 4,816,670 | A | 3/1989 | Kitamura et al. |
| 4,817,601 | A | 4/1989 | Roth et al. |
| 4,834,493 | A * | 5/1989 | Cahill et al. ............ 385/77 |
| 4,889,129 | A | 12/1989 | Dougherty et al. |
| 4,968,314 | A | 11/1990 | Michaels |
| 4,979,797 | A | 12/1990 | Nemeth |
| 4,985,029 | A | 1/1991 | Hoshino |
| 4,988,163 | A | 1/1991 | Cohen et al. |
| 4,995,691 | A | 2/1991 | Purcell, Jr. |
| 5,011,254 | A | 4/1991 | Edwards et al. |
| 5,011,279 | A | 4/1991 | Auweter et al. |
| 5,026,366 | A | 6/1991 | Leckrone et al. |
| 5,037,180 | A | 8/1991 | Stone |
| 5,037,421 | A | 8/1991 | Boutacoff et al. |
| 5,041,109 | A | 8/1991 | Abela |
| 5,042,980 | A | 8/1991 | Baker et al. |
| 5,074,632 | A | 12/1991 | Potter |
| 5,093,877 | A | 3/1992 | Aita et al. |
| 5,100,507 | A | 3/1992 | Cholewa et al. |
| 5,112,127 | A | 5/1992 | Carrabba et al. |
| 5,129,896 | A | 7/1992 | Hasson |
| 5,146,917 | A | 9/1992 | Wagnieres et al. |
| 5,147,353 | A | 9/1992 | Everett |
| 5,147,354 | A | 9/1992 | Boutacoff et al. |
| 5,151,096 | A | 9/1992 | Khoury |
| 5,154,708 | A | 10/1992 | Long et al. |
| 5,164,945 | A | 11/1992 | Long et al. |
| 5,166,756 | A | 11/1992 | McGee et al. |
| 5,188,635 | A | 2/1993 | Radtke |
| 5,190,536 | A | 3/1993 | Wood et al. |
| 5,193,526 | A | 3/1993 | Daikuzono |
| 5,196,005 | A | 3/1993 | Doiron et al. |
| 5,207,669 | A | 5/1993 | Baker et al. |
| 5,253,312 | A | 10/1993 | Payne et al. |
| 5,254,114 | A | 10/1993 | Reed, Jr. et al. |
| 5,263,951 | A | 11/1993 | Spears et al. |
| 5,263,952 | A | 11/1993 | Grace et al. |
| 5,267,995 | A | 12/1993 | Doiron et al. |
| 5,269,777 | A * | 12/1993 | Doiron et al. ............ 606/7 |
| 5,290,275 | A | 3/1994 | Kittrell et al. |
| 5,292,320 | A | 3/1994 | Brown et al. |
| 5,300,066 | A | 4/1994 | Manoukian et al. |
| 5,306,274 | A | 4/1994 | Long |
| 5,330,465 | A | 7/1994 | Doiron et al. |
| 5,343,543 | A | 8/1994 | Novak, Jr. et al. |
| 5,349,590 | A | 9/1994 | Amirkhanian et al. |
| 5,352,221 | A | 10/1994 | Fumich |
| 5,354,294 | A | 10/1994 | Chou |
| 5,370,649 | A | 12/1994 | Gardeto et al. |
| 5,401,270 | A | 3/1995 | Muller et al. |
| 5,402,508 | A | 3/1995 | O'Rourke et al. |
| 5,404,218 | A | 4/1995 | Nave et al. |
| 5,415,655 | A | 5/1995 | Fuller et al. |
| 5,421,928 | A | 6/1995 | Knecht et al. |
| 5,428,699 | A * | 6/1995 | Pon ............ 385/31 |
| 5,432,880 | A | 7/1995 | Diner |
| 5,445,608 | A | 8/1995 | Chen et al. |
| 5,495,541 | A * | 2/1996 | Murray et al. ............ 385/33 |
| 5,509,917 | A * | 4/1996 | Cecchetti et al. ............ 606/15 |
| 5,534,000 | A * | 7/1996 | Bruce ............ 606/15 |
| 5,536,265 | A | 7/1996 | van den Bergh et al. |
| 5,562,657 | A | 10/1996 | Griffin |
| 5,631,986 | A | 5/1997 | Frey et al. |
| 5,643,253 | A | 7/1997 | Baxter et al. |
| 5,662,646 | A | 9/1997 | Fumich |
| 5,688,263 | A | 11/1997 | Hauptmann et al. |
| 5,693,043 | A | 12/1997 | Kittrell et al. |
| 5,695,583 | A | 12/1997 | van den Bergh et al. |
| 5,710,626 | A | 1/1998 | O'Rourke et al. |
| 5,717,807 | A | 2/1998 | Theroux et al. |
| 5,725,521 | A | 3/1998 | Mueller |
| 5,728,091 | A | 3/1998 | Payne et al. |
| 5,754,717 | A | 5/1998 | Esch |
| 5,764,840 | A | 6/1998 | Wach |
| 5,807,389 | A | 9/1998 | Gardetto et al. |
| 5,843,073 | A | 12/1998 | Sinofsky |
| 5,868,734 | A | 2/1999 | Soufiane et al. |
| 5,878,178 | A | 3/1999 | Wach |
| 5,897,551 | A * | 4/1999 | Everett et al. ............ 606/15 |
| 5,908,415 | A | 6/1999 | Sinofsky |
| 5,947,959 | A | 9/1999 | Sinofsky |
| 5,991,404 | A | 11/1999 | Brahami et al. |
| 6,033,398 | A | 3/2000 | Farley et al. |
| 6,102,905 | A * | 8/2000 | Baxter et al. ............ 606/15 |
| 6,164,280 | A | 12/2000 | Everett et al. |
| 6,270,492 | B1 | 8/2001 | Sinofsky |
| 6,270,495 | B1 | 8/2001 | Palermo |
| 6,344,048 | B1 | 2/2002 | Chin et al. |
| 6,352,549 | B1 | 3/2002 | Everett |
| 6,375,651 | B2 * | 4/2002 | Grasso et al. ............ 606/15 |
| 6,398,777 | B1 | 6/2002 | Navarro et al. |
| 6,522,806 | B1 | 2/2003 | James, IV et al. |
| 6,555,827 | B1 | 4/2003 | Kockott |
| 6,561,998 | B1 | 5/2003 | Roth et al. |

(56) References Cited

U.S. PATENT DOCUMENTS

| | | | |
|---|---|---|---|
| 6,767,338 | B2 | 7/2004 | Hawk et al. |
| 6,796,710 | B2 | 9/2004 | Yates et al. |
| 6,986,766 | B2 * | 1/2006 | Caldera et al. .................. 606/15 |
| 7,063,695 | B2 | 6/2006 | Nield et al. |
| 7,267,674 | B2 | 9/2007 | Brucker et al. |
| 7,273,478 | B2 | 9/2007 | Appling et al. |
| 7,284,981 | B2 | 10/2007 | Schmid et al. |
| 7,331,954 | B2 | 2/2008 | Temelkuran et al. |
| 7,412,132 | B1 * | 8/2008 | Liu et al. ......................... 385/34 |
| 2002/0183729 | A1 * | 12/2002 | Farr et al. ........................ 606/15 |
| 2003/0078568 | A1 * | 4/2003 | Caldera et al. .................. 606/15 |
| 2004/0044337 | A1 * | 3/2004 | Shafirstein et al. ............. 606/28 |
| 2005/0015123 | A1 * | 1/2005 | Paithankar ...................... 607/88 |
| 2005/0131400 | A1 * | 6/2005 | Hennings et al. ............... 606/15 |
| 2005/0203497 | A1 * | 9/2005 | Speeg et al. ..................... 606/15 |
| 2005/0244101 | A1 * | 11/2005 | Kitabayashi et al. ........... 385/33 |
| 2006/0189967 | A1 | 8/2006 | Masotti et al. |
| 2007/0167937 | A1 * | 7/2007 | Brown ............................ 606/15 |
| 2007/0179485 | A1 * | 8/2007 | Yeik et al. ....................... 606/15 |
| 2008/0015559 | A1 | 1/2008 | Appling et al. |

OTHER PUBLICATIONS

PCT International Search Report for PCT/US2008/059791 dated Nov. 4, 2008.

* cited by examiner

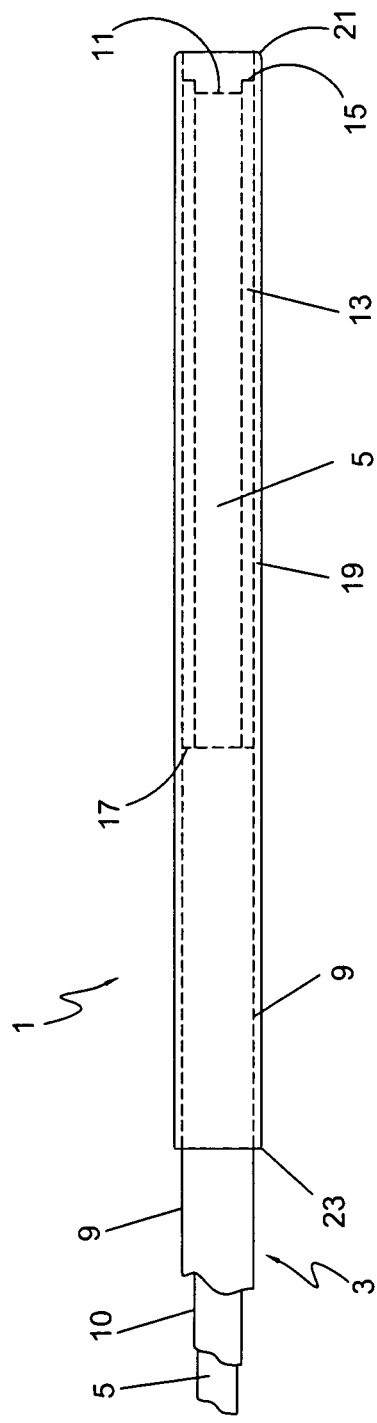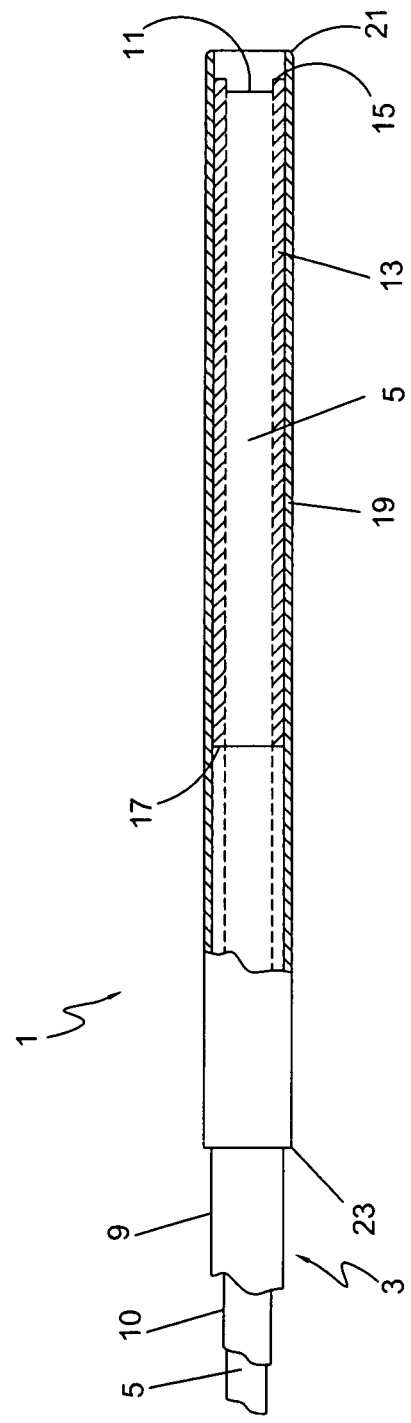

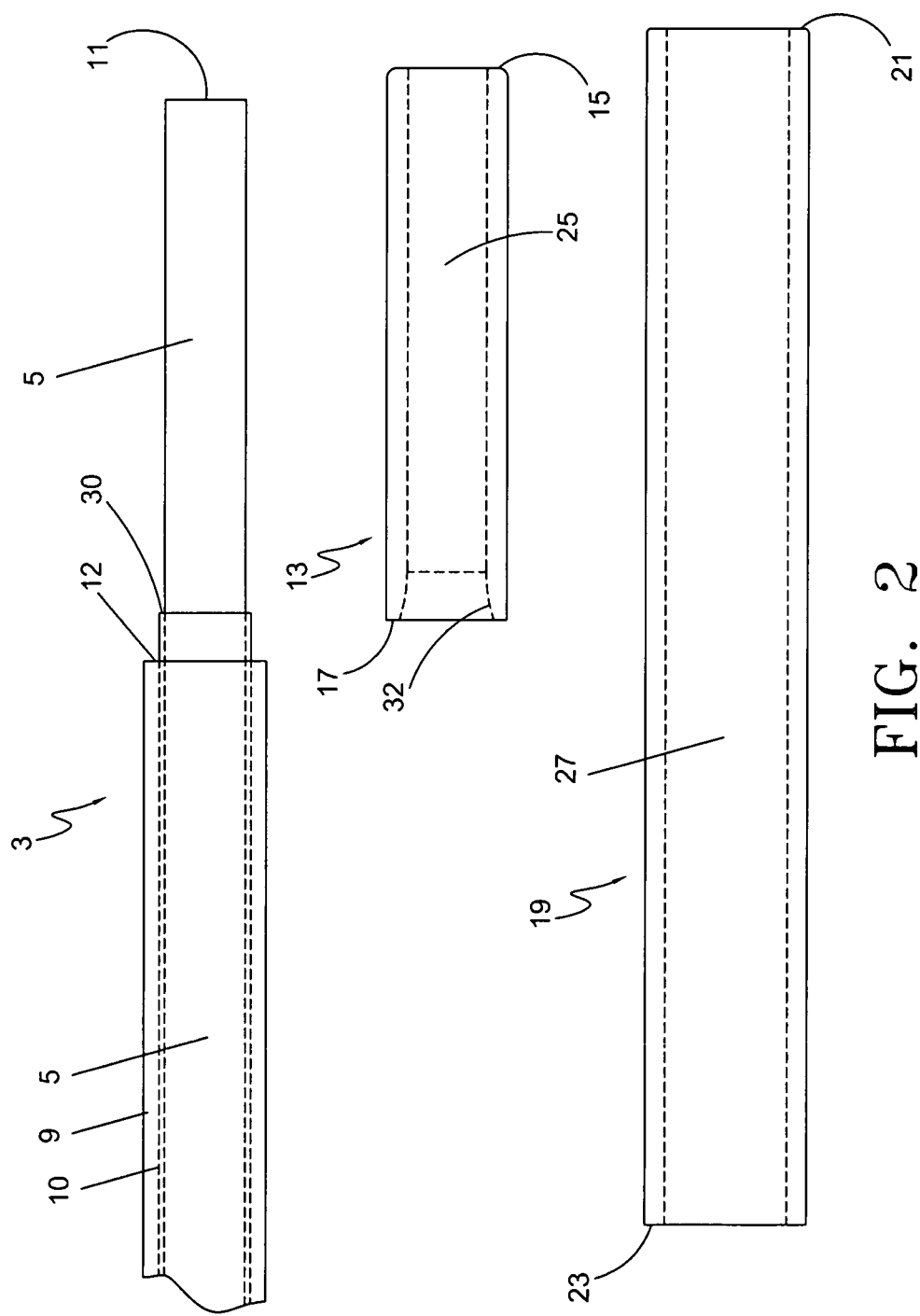

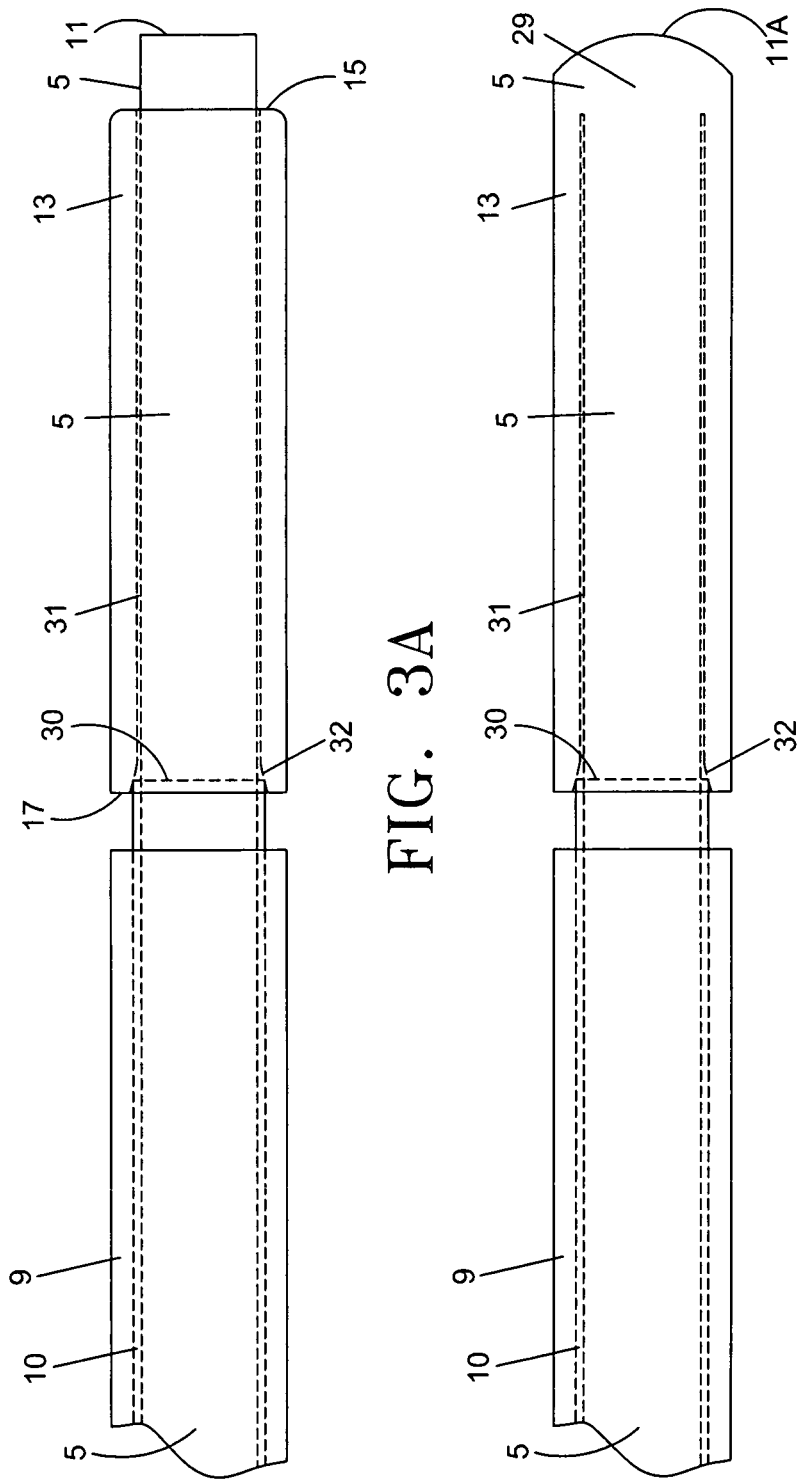

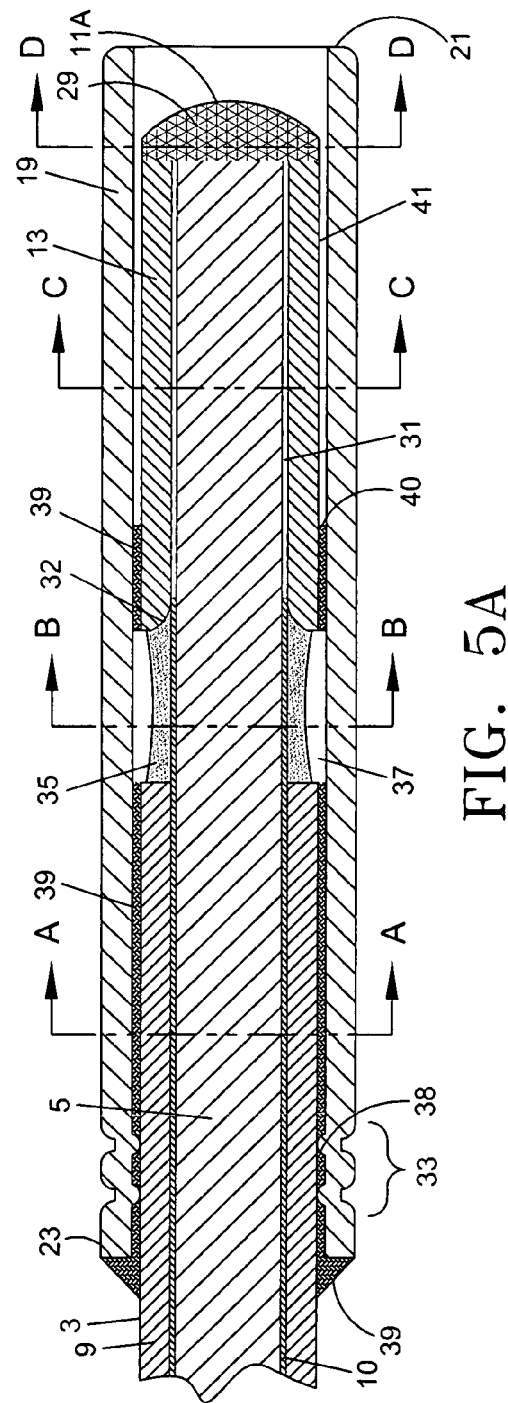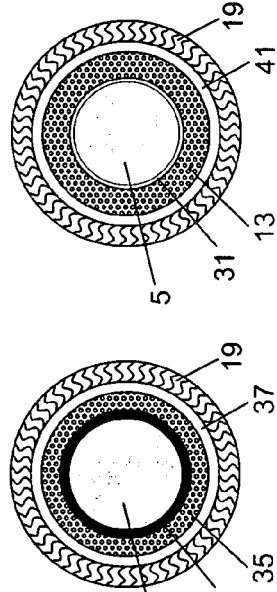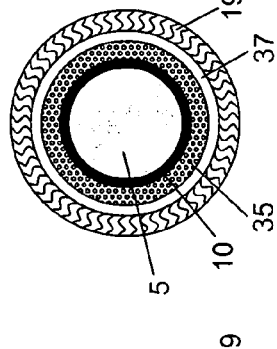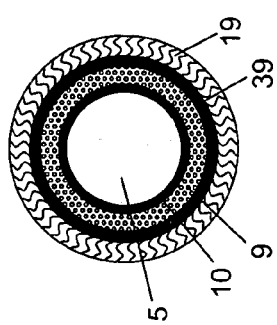
FIG. 5A   FIG. 5B   FIG. 5C   FIG. 5D   FIG. 5E

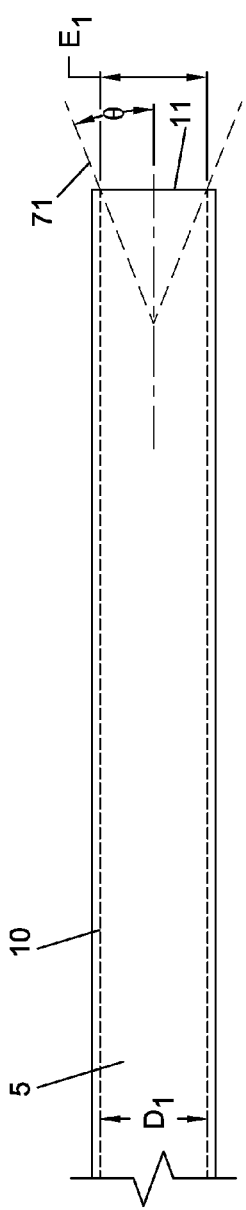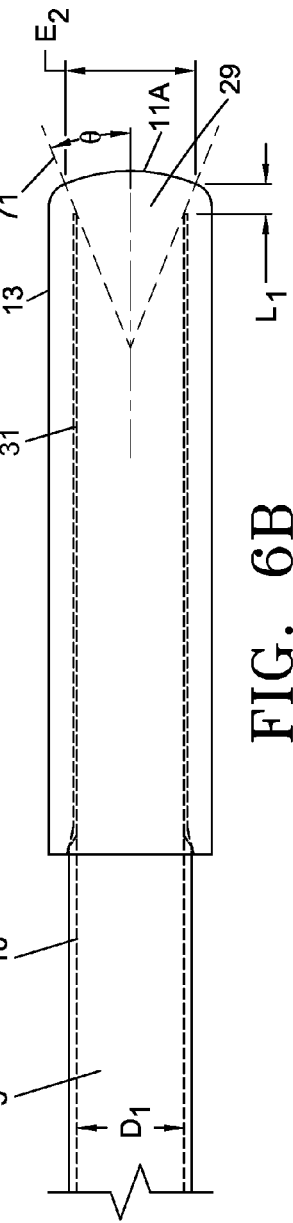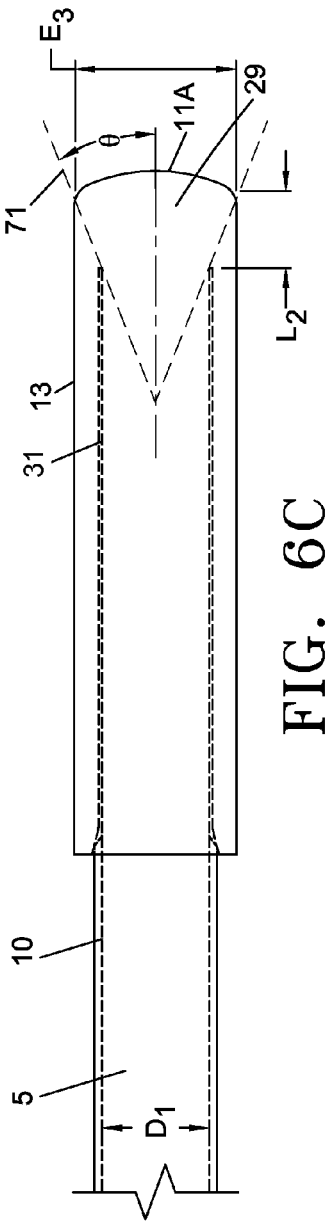
FIG. 6A PRIOR ART
FIG. 6B
FIG. 6C

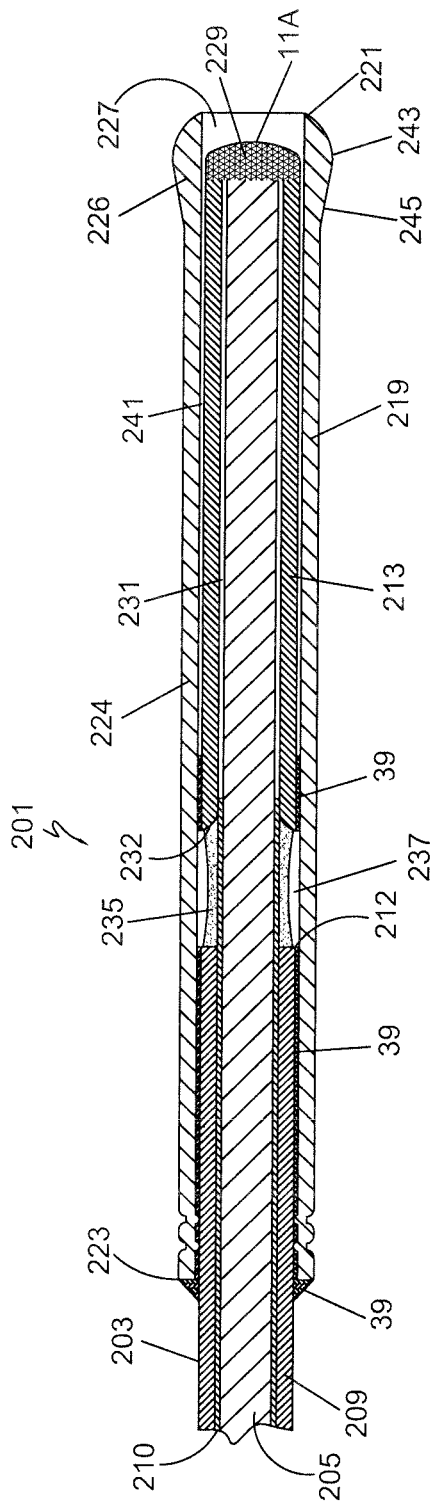

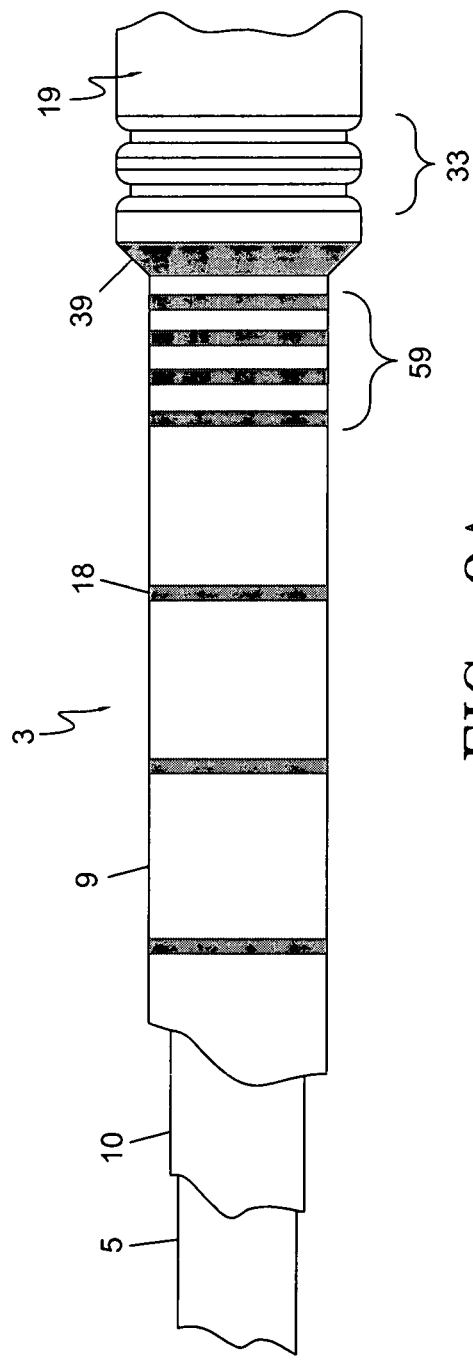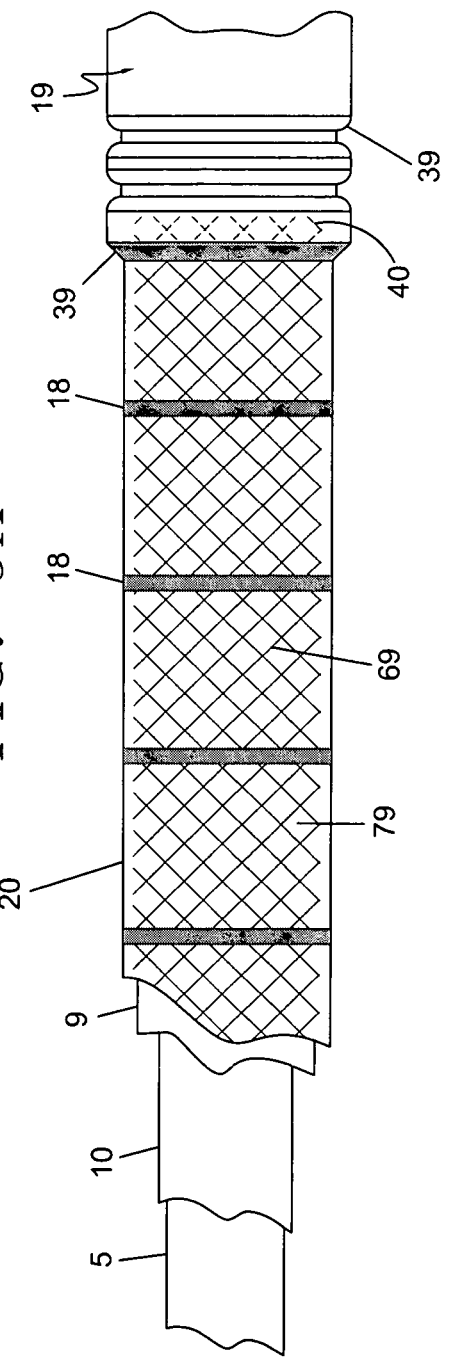
FIG. 9A
FIG. 9B

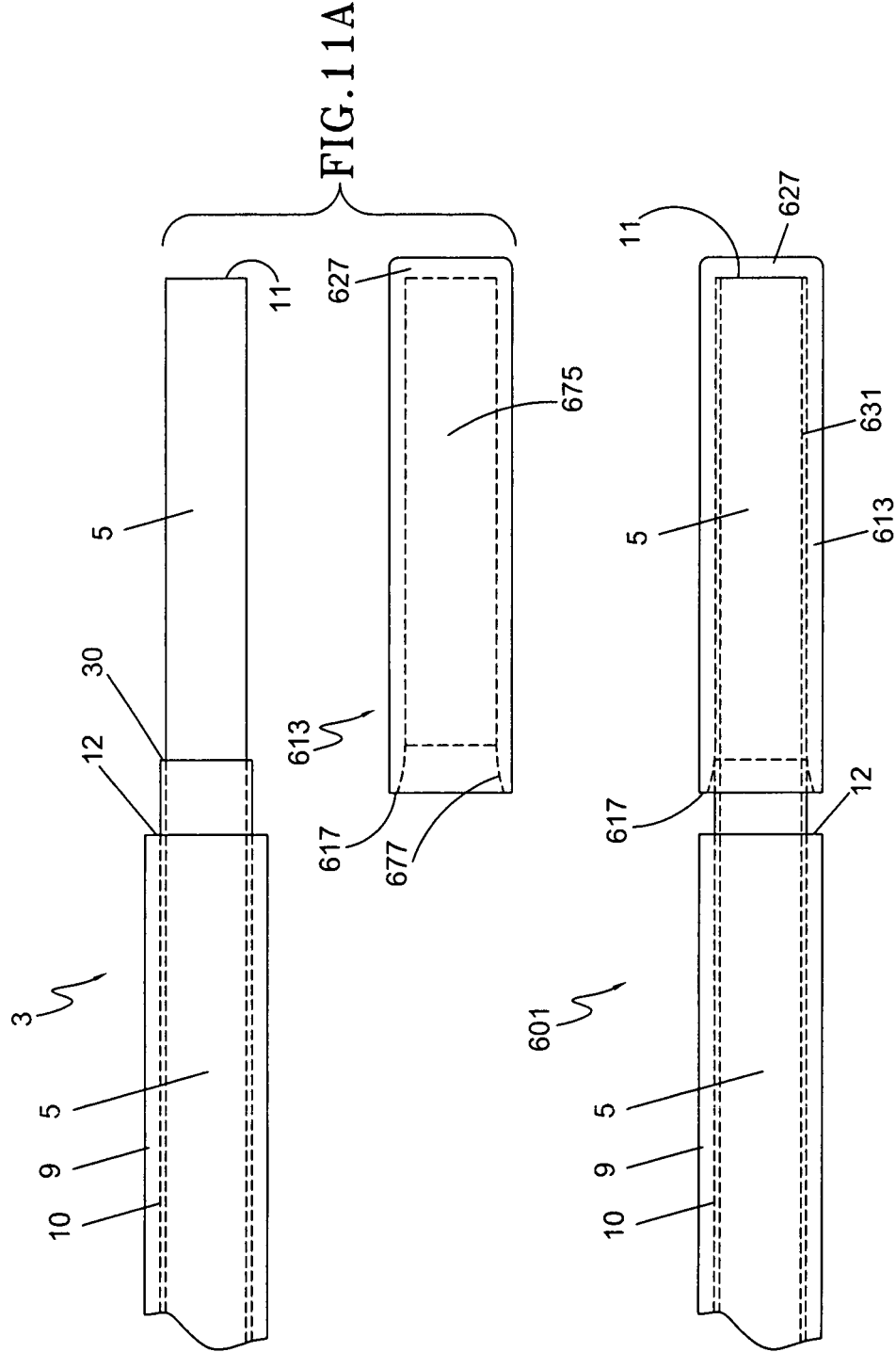

DEVICE AND METHOD FOR ENDOVASCULAR TREATMENT FOR CAUSING CLOSURE OF A BLOOD VESSEL

CROSS REFERENCE TO RELATED APPLICATIONS

This application claims priority under 35 U.S.C. Section 119(e) to U.S. Provisional Application Ser. No. 60/910,743, filed Apr. 9, 2007, U.S. Provisional Application Ser. No. 60/913,767, filed Apr. 24, 2007, and U.S. Provisional Application Ser. No. 60/969,345, filed Aug. 31, 2007, all of which are incorporated herein by reference.

FIELD OF THE INVENTION

The present invention relates to a medical device and method for treating blood vessels, and more particularly to a laser treatment device and method for causing closure of varicose veins.

BACKGROUND OF THE INVENTION

Veins are thin-walled and contain one-way valves that control blood flow. Normally, the valves open to allow blood to flow into the deeper veins and close to prevent back-flow into the superficial veins. When valves are malfunctioning or only partially functioning, however, they no longer prevent the back-flow of blood into the superficial veins. As a result, venous pressure builds at the site of the faulty valves. Because the veins are thin walled and not able to withstand the increased pressure, they become what are known as varicose veins which are veins that are dilated, tortuous or engorged.

In particular, varicose veins of the lower extremities is one of the most common medical conditions of the adult population. It is estimated that varicose veins affect approximately 25% of adult females and 10% of males. Symptoms include discomfort, aching of the legs, itching, cosmetic deformities, and swelling. If left untreated, varicose veins may cause medical complications such as bleeding, phlebitis, ulcerations, thrombi and lipderatosclerosis.

Endovascular thermal therapy is a relatively new treatment technique for venous reflux diseases such as varicose veins. With this technique, the thermal energy is delivered by a flexible optical fiber or radiofrequency electrode that is percutaneously inserted into the diseased vein prior to energy delivery. For laser delivery, a treatment sheath is typically inserted into the vein at a distal location and advanced to within a few centimeters of the source of reflux. Once the treatment sheath is properly positioned, a flexible optical fiber is inserted into the lumen of the treatment sheath and advanced until the fiber tip is near the treatment sheath tip but still protected within the sheath lumen.

Prior to laser activation, the treatment sheath is withdrawn approximately 1-4 centimeters to expose the distal tip of the optical fiber. After the fiber tip has been exposed a selected distance beyond the treatment sheath tip, a laser generator is activated causing laser energy to be emitted from the bare flat tip of the fiber into the vessel. The emitted energy heats the blood causing hot bubbles of gas to be created. The gas bubbles transfer thermal energy to the vein wall, causing cell necrosis, thrombosis and eventual vein collapse. With the laser generator turned on, both the optical fiber and treatment sheath are slowly withdrawn as a single unit until the entire diseased segment of the vessel has been treated.

A typical laser system uses a 600-micron optical fiber covered with a polymer jacket and cladding layer. The fiber core extends through the fiber terminating in an energy emitting face.

With some prior art treatment methods, contact between the energy-emitting face of the fiber optic tip and the inner wall of the varicose vein is recommended to ensure complete collapse of the diseased vessel. For example, U.S. Pat. No. 6,398,777, issued to Navarro et al, teaches either the means of applying pressure over the laser tip or emptying the vessel of blood to ensure that there is contact between the vessel wall and the fiber tip. One problem with direct contact between the laser fiber tip and the inner wall of the vessel is that it can result in vessel perforation and extravasation of blood into the perivascular tissue. This problem is documented in numerous scientific articles including "Endovenous Treatment of the Greater Saphenous Vein with a 940-nm Diode Laser: Thrombotic Occlusion After Endoluminal Thermal Damage By Laser-Generated Steam Bubble" by T. M. Proebstle, MD, in Journal of Vascular Surgery, Vol. 35, pp. 729-736 (April, 2002), and "Thermal Damage of the Inner Vein Wall During Endovenous Laser Treatment: Key Role of Energy Absorption by Intravascular Blood" by T. M. Proebstle, MD, in Dermatol Surg, Vol. 28, pp. 596-600 (2002), both of which are incorporated herein by reference. When the fiber contacts the vessel wall during treatment, intense direct laser energy is delivered to the vessel wall rather than indirect thermal energy from the gas bubbles from heating of the blood. Laser energy in direct contact with the vessel wall causes the vein to perforate at the contact point and surrounding area. Blood escapes through these perforations into the perivascular tissue, resulting in post-treatment bruising and associated discomfort.

Another problem created by the prior art methods involving contact between the fiber tip and vessel wall is that inadequate energy is delivered to the non-contact segments of the diseased vein. Inadequately heated vein tissue may not occlude, necrose or collapse, resulting in incomplete treatment. With the fiber tip in contact with the vessel wall rather than the bloodstream, hot gas bubbles are not created. The bubble is the mechanism by which the 360 degree circumference of the vessel wall is damaged. Without the bubbles, it is possible for some vein tissue to be under heated or not heated at all, resulting in incomplete treatment and possible recanalization of the vessel.

A related problem with endovascular laser treatment of varicose veins using a conventional fiber device is fiber tip damage during laser energy emission caused by localized heat build up at the working end of the fiber, which may lead to thermal runaway. Thermal runaway occurs when temperature at the fiber tip reaches a threshold where the core and/or cladding begin to absorb the laser radiation. As the fiber begins to absorb the laser energy it heats more rapidly, quickly spiraling to the point at which the emitting face begins to burn back like a fuse. One cause of the heat build up is the high power density at the emitting face of the fiber. A conventional fiber includes a cladding layer immediately surrounding the fiber core. Laser energy emitted from the distal end of the device may create thermal spikes with temperatures sufficiently high to cause the cladding layer to burn back. Once the cladding layer is no longer present, laser energy will travel through the side wall of the fiber, causing additional energy loss and localized heating. The fiber weakens under the high temperatures and may break.

In a related problem with conventional endovenous laser treatment methods, numerous procedural steps and accessory components are required to correctly position the optical fiber at the treatment site prior to the application of laser energy. The procedure is time-consuming and expensive partially due to the costs of the accessory components, which includes a treatment sheath designed to provide a pathway for the fiber to be advanced through the vessel to the source of reflux. The introduction of multiple components including the treatment sheath requires a large access site puncture which may result in patient complications including bruising, prolonged bleeding, scarring, and infection.

Therefore, it would be desirable to provide an endovascular treatment device and method that protects the emitting face of the optical fiber from direct contact with the inner wall of vessel during the emission of laser energy to ensure consistent thermal heating across the entire vessel circumference thus avoiding vessel perforation and/or incomplete vessel collapse.

It is also desirable to provide an endovascular treatment device and method which decreases peak temperatures at the working end of the fiber during the emission of laser energy thus avoiding the possibility of fiber damage and/or breakage due to heat stress caused by thermal runaway.

It is yet another purpose to provide an endovascular treatment device and method which reduces the number of accessory components and procedural steps required to successfully treat a blood vessel.

Various other purposes and embodiments of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention may be found in the Detailed Description of the Invention.

SUMMARY OF THE INVENTION

According to one aspect of the present invention, an endovascular laser treatment device for causing closure of a blood vessel is provided. The treatment device uses an optical fiber having a core through which a laser light travels and is adapted to be inserted into a blood vessel. An inner sleeve is arranged around a distal portion of the core such that both distal ends of the inner sleeve and the optical fiber core form an enlarged light emitting face. An outer sleeve is arranged around the inner sleeve. The outer sleeve acts as a spacer to position the light emitting face away from an inner wall of the blood vessel.

As can be appreciated, the enlarged light emitting face provides substantially lower power density while providing the same amount of total energy during a treatment session. The reduced power density reduces peak temperatures near the emitting face and prevents thermal runaway and device damage. The reduced average power density from the enlarged emitting face and the spacing of the emitting face away from the vessel wall due to the outer sleeve both serve to reduce the possibility of vessel perforations, leading to less bruising, post-operative pain and other clinical complications.

In another aspect of the invention, an endovascular treatment method for causing closure of a blood vessel is provided. The method involves inserting into a blood vessel an optical fiber having a core and a spacer sleeve arranged around a distal portion of the core. The distal end of the fiber core defines a light emitting face. Once the optical fiber is inserted, a laser light is applied through the light emitting face while the inserted optical fiber and spacer sleeve are moved longitudinally to treat a defined segment of the blood vessel. The application of laser light causes closure of the blood vessel. Advantageously, the spacer sleeve positions the light emitting face away from an inner wall of the blood vessel, thereby reducing the possibility of vessel wall perforations and less bruising.

In yet another aspect of the present invention, the spacer comprises an inner sleeve and an outer sleeve both arranged around a distal portion of the core to prevent the laser light from traveling laterally and to position the light emitting face away from an inner wall of the vessel. The inner sleeve can be a heat resistive material such as ceramic and the outer sleeve can be, for example, a metallic sleeve to provide structural integrity and strength to the distal section of the treatment device. The outer sleeve can be especially important when the inner sleeve is a ceramic material. Because the ceramic material is brittle, portions of the material can come apart due to heat stress and the outer sleeve surrounding the inner sleeve can help dissipate heat and prevent loose ceramic parts from traveling into the blood vessel, which can be very dangerous.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 1A is a longitudinal plan view of the distal section of the optical fiber with spacer assembly.

FIG. 1B is a partial cross-sectional view of the distal section of the optical fiber with spacer assembly.

FIG. 2 depicts longitudinal plan views of the components of the distal section of the fiber with spacer assembly prior to assembly including the optical fiber, the inner glass sleeve and the outer protective sleeve.

FIG. 3A is a partial plan view of the distal section of the fiber and inner glass sleeve subassembly prior to fusing.

FIG. 3B is a partial plan view of the distal section of the fiber with inner glass sleeve subassembly after fusing of the distal end.

FIG. 5A illustrates a detailed longitudinal cross-sectional view of the distal section of the optical fiber with spacer assembly.

FIG. 5B through 5E are cross-sections of FIG. 5A taken along lines A-A, B-B, C-C and D-D.

FIG. 6A is a partial plan view of the distal section of a conventional prior art fiber illustrating the maximum propagation angle θ of the laser beam given an emitting face diameter of $E_1$.

FIG. 6B is a partial plan view of the distal section of the optical fiber/inner glass sleeve subassembly illustrating the relationship between weld length $L_1$ and an increase in surface area of the emitting face $E_2$.

FIG. 6C is a partial plan view of the distal section of the optical fiber/inner glass sleeve assembly illustrating the relationship between weld length $L_2$ and an increase in surface area of the emitting face $E_3$.

FIG. 8A is a partial longitudinal cross-sectional view of the distal segment of an alternative embodiment of an optical fiber with spacer assembly.

FIG. 8B is an end view of the embodiment of FIG. 8A shown from the distal end of the device.

FIG. 9A is a partial plan view of a one embodiment of the fiber shaft illustrated with the distal section of the outer protective sleeve.

FIG. 9B is partial plan view of another embodiment of the fiber shaft illustrated with the distal section of the outer protective sleeve.

FIG. 11A depicts a partial plan view of the distal section of the fiber with a plan view of an alternative embodiment of the inner glass sleeve.

FIG. 11B illustrates the subassembly of the fiber and inner glass sleeve of FIG. 11A.

DETAILED DESCRIPTION OF THE INVENTION

Figure 4:
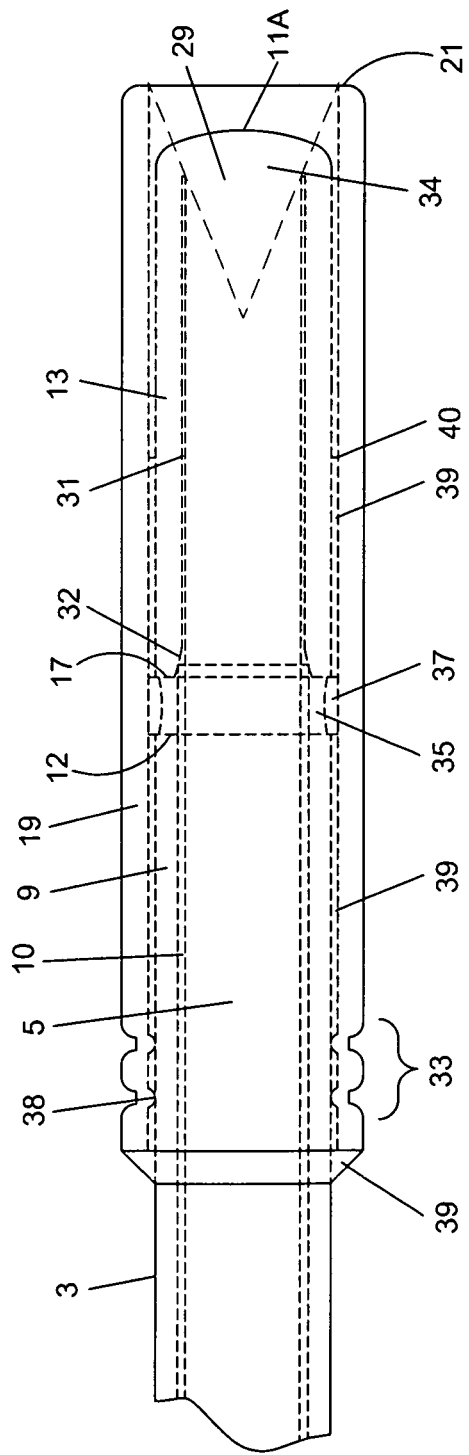
FIG. 4 is a partial plan view of the distal section of the fiber, inner glass sleeve assembled with the outer protective sleeve.

The following detailed description should be read with reference to the drawings, in which like elements in different drawings are identically numbered. The drawings, which are not necessarily to scale, depict selected preferred embodiments and are not intended to limit the scope of the claims. The detailed description illustrates by way of example, not by way of limitation, the principles of the invention. In various embodiments, and referring to FIGS. 1-14, presented herein are exemplary devices and methods for endovenous laser treatment. FIGS. 1A and 1B illustrate the distal section of one embodiment of the optical fiber with spacer assembly 1 from a partial plan view and partial cross-sectional view, respectively. Optical fiber with spacer assembly 1 is comprised of an optical fiber 3, an insulative inner sleeve 13 and an optional outer protective sleeve 19 coaxially surrounding the inner insulative sleeve 13 and the distal portion of the optical fiber 3. The spacer assembly includes the inner sleeve 13 and outer sleeve 19. The optical fiber 3 is comprised of a core 5, cladding layer 10 and a protective fiber jacket 9 surrounding the cladding layer 10. As disclosed herein, the fiber core may range from 200-1000 microns in diameter. In one exemplary aspect, the core 5 is 600 microns.

The protective jacket 9, which can be susceptible to burnback during operation, may be stripped back from the emitting face 11 of the fiber 3 for a length of approximately 9 mm to where the proximal edge 17 of insulative inner sleeve 13 abuts up against protective jacket 9 of the fiber 3. Outer protective sleeve 19 extends from its distal most edge 21 proximally over the fiber core 5 and a portion of the cladding and jacketed section of the fiber 3, terminating in proximal end 23.

In the embodiment shown in FIGS. 1A and 1B, the front emitting face 11 of optical fiber 3 is recessed from the distal end 15 of insulative inner sleeve 13 and further recessed from the distal end 21 of protective spacer sleeve 19. This configuration, with its heat insulating properties helps to reduce temperatures at the distal end of the device, in turn preventing thermal runaway and possible melting of the core. In addition, the multi-layer design acts as a spacer to prevent contact between the front emitting face 11 of the fiber 3 and the vessel wall, as will be explained in more detail below.

In one exemplary aspect, the axial distance between the energy emitting face 11 of the optical fiber 3 and the distal end 15 of the insulative inner glass sleeve after assembly is approximately 0.006 inches. This distance may range from flush with the emitting face 11 to approximately 0.024 inches and may be in one aspect from about 0.003 inches to about 0.024 inches. Generally, the distance is equal to approximately half the cross-sectional diameter of the fiber core 5. The insulative inner sleeve 13 functions as a spacer by preventing any laser energy from being emitted from the side wall of the fiber core 5. Inner insulative sleeve 13 minimizes heat transmission at the distal end of the device, as will be described in more detail below. In the embodiment depicted in FIGS. 1A and 1B, the inner insulative sleeve 13 may be ceramic or other type of high-temperature resistant materials such as, but not limited to carbon or silica while the outer sleeve 19 may be a metallic sleeve such as a stainless steel sleeve to provide structural integrity to the spacer assembly and enhanced ultrasound visibility.

In one exemplary aspect, the axial distance between the distal end of the energy emitting face 11 and distal end 21 of the outer protective sleeve 19 after assembly is approximately 0.024 inches. This distance can range from about 0 to about 0.030 inches, and in one aspect, from about 0.005 inches to 0.024 inches. Generally, the distance between the emitting face 11 and the distal end 21 of the outer protective sleeve 19 should be selected such that the light emitted from the fiber emitting face 11 does not contact the inner wall of the outer protective sleeve 19 as it is transmitted from the energy emitting face 11 of the fiber 3 to the blood vessel lumen.

The distal end 21 of the outer protective sleeve 19 may extend approximately 0.006 inches beyond the distal end 15 of the insulative sleeve 13 and approximately 0.012 inches beyond the distal end of the energy emitting face 11. Alternatively, in another aspect, the distal end 21 of the outer protective sleeve 19 may be positioned flush with the energy emitting face 11. In this aspect, the insulative inner glass sleeve 13 may extend distally beyond the energy emitting face 11 to shield the fiber core 5, thereby protecting the vessel wall from inadvertent contact with the fiber core 5 emitting face 11.

FIG. 2 depicts the distal section of the components of an alternative embodiment of optical fiber with spacer assembly 1. The distal end section includes optical fiber 3, an inner glass sleeve 13 and a protective outer sleeve 19 prior to assembly. In one exemplary aspect, the fiber may be a 600 micron fiber, the core 5 may about 0.0239 inches in diameter and coaxially surrounded by a thin cladding layer 10 with a wall thickness of approximately 0.0003 inches. Where the cladding 10 is present, the outer diameter of the fiber 3 may be approximately 0.0246 inches. With the addition of the protective jacket layer 9, the overall outer diameter of the fiber 3 is about 0.041 inches. The optical fiber 3 is shown with the protective jacket 9 removed from the distal emitting face 11 to point 12. The cladding layer 10 is removed from the distal face 11 to point 30. The distance between the leading edge 12 of the protective jacket layer 9 and the leading edge 30 of the cladding 10 may be between approximately 0.25 mm and 2.00 mm in length. In one exemplary aspect, the optical fiber 3 has a silica core and a polymer cladding layer (e.g., fluoropolymer). In this aspect, both the jacket 9 and cladding layer 10 are stripped as shown in FIG. 2. In another aspect, the optical fiber may have a glass core 5 and a glass (e.g., doped silica) cladding layer 10. In this aspect, only the jacket 9 is stripped back, although the glass cladding layer 10 may also be stripped.

As illustrated in FIG. 2, the inner glass sleeve 13 may be comprised of silica ($SiO_2$) or other glass or quartz material compositions with an index of refraction equivalent or close to that of the fiber core 5. Having index-matching materials reduces the Fresnel reflection, which minimizes emission of laser energy through the side surfaces of the core by redirecting the laser beam in a forward direction, as is known in the art.

In one embodiment, the inner sleeve 13 may be approximately 0.236 inches in length. A through lumen 25 extends from the distal edge 15 of the inner glass sleeve 13 to terminate at proximal edge 17. The outer diameter of the inner glass sleeve 13 may be approximately 0.041 inches in order to ensure that the outer surface of inner sleeve 13 is flush with the outer surface of the unstripped portion of optical fiber 3 after assembly, as shown in FIGS. 1A and 1B. The through lumen 25 is dimensioned so as to allow the stripped portion of the optical fiber 3 to be inserted into and through the inner glass sleeve 13. For a standard 600 micron fiber, the lumen 25 of inner glass sleeve 13 may be dimensioned at about 0.0243 inches to accommodate a fiber core 5 diameter of approximately 0.0239 inches. In the embodiment shown, the proximal edge 17 of inner glass sleeve 13 has an expanded luminal diameter which tapers inwardly from a diameter of approximately 0.0280 inches to the nominal through lumen diameter of about 0.0243 inches. The internally tapered wall 32 provides for ease of assembly when inserting the fiber core 5 into the inner glass sleeve 13. It also allows for insertion of the leading edge 30 of cladding 10 into the sleeve lumen 25 to create an overlapping seal with the inner glass sleeve 13, as is shown more clearly in FIG. 3A.

In one aspect, as illustrated in FIG. 2, outer protective sleeve 19 is an optional element that may be included in the assembly. Outer protective sleeve 19 is designed to space the energy emitting end 11 of the fiber away from the vessel wall to increase the durability of the distal region of the optical fiber assembly 1, and to enhance tracking through the vessel during the insertion. In one aspect, sleeve 19 may be comprised of a heat conductive metal such as medical grade stainless steel, gold, platinum, or nitinol. These materials will dissipate heat. Alternatively, sleeve 19 may be comprised of heat-resistant materials such as ceramic, high-temperature polymer, carbon or silica. Heat-resistant materials minimize heat transmission to the surface of the sleeve. A combination of heat-conductive and heat-resistant materials may also be used to construct the distal end section of the fiber.

Inherently, a multilayer structure as disclosed herein will increase the visibility of the distal end of device 1 under ultrasound or other imaging modality. The sleeve 19 may be coated with a lubricous substance to enhance trackability through the vessel. Outer protective sleeve 19 may also be coated with a substance, such as titanium nitride (TiN) or gold, to reduce friction between the sleeve 19 and the vessel wall when the distal end of the device increases in temperature, as will be described in more detail below.

In one aspect, outer protective sleeve 19 includes through lumen 27 that extends from distal edge 21 to proximal edge 23. The diameter of lumen 27 may be is approximately 0.042 inches so as to allow a snug fit when assembled coaxially over the inner glass sleeve 13, which in one exemplary aspect, may have an outer diameter of approximately 0.041 inches. The outer protective sleeve 19 may be approximately 1.6 cm in length, and when assembled with the fiber 3 and inner glass sleeve 13, extends proximally past the bare fiber section to coaxially surround the distal section of the outer protective jacket 9. The distal end 21 of outer protective sleeve 19 may be radiused or have an expanded diameter to enhance trackability, as will be discussed in more detail below.

FIGS. 3A, 3B and FIG. 4 illustrate the assembly steps for the optical fiber with spacer assembly 1. As depicted in FIG. 3A, the first step in the assembly process is to assemble the fiber 3 to the inner glass sleeve 13. Leading edge 17 of inner sleeve 13 is first slid over the energy emitting face 11 of the optical fiber 3 and advanced until the internal taper 32 of inner sleeve 13 contacts the leading edge 30 of the cladding 10. Inner sleeve 13 is advanced over the fiber core 5 until the leading edge 30 of cladding 10 is positioned within the lumen 25 at internal sleeve taper 32. Once the inner diameter of the taper 32 reaches about 0.0248 inches, the fiber 3 with cladding 10 is prevented from further advancement due to an interference fit, resulting in a small overlap between the cladding 10 and inner glass sleeve 13. The interference fit and overlap between these two components helps to maintain the position of the inner glass sleeve 13 on the fiber 3 during the next assembly step and also to seal off the proximal opening of lumen 25 of inner sleeve 13.

In one aspect of the assembly 1, as shown in FIG. 3A, an annular constant-width air gap 31 is created between the inner glass sleeve 13 and the fiber core 5. The air gap 31 may be about 0.0002 inches wide for a 600 micron fiber assembly, based on a core 5 diameter of 0.0239 inches and an inner sleeve 13 diameter of 0.0243 inches. At this stage of the assembly process, air gap 31 extends longitudinally from the leading edge 15 of inner sleeve 13 to the front face 30 of the cladding 10. The interference fit between the leading edge 30 of cladded fiber 10 and the tapered section 32 of inner glass sleeve 13 creates a seal, effectively closing off the proximal opening of air gap 31. In one aspect, the front emitting face 11 of the fiber core 5 may extend distally from the leading edge 15 of the inner glass sleeve 13. In one embodiment of a 600 micron fiber, the fiber core 5 may extend approximately 1.5 mm distally of the inner glass sleeve 13.

Once the inner glass sleeve 13 is properly aligned over the fiber 3, the distal end 15 of inner sleeve 13 is welded or fused together with the energy-emitting face 11 of the bare fiber core 5 to form distal end section 29, as shown in FIG. 3B. In one aspect, both the fiber core 5 and the inner glass sleeve are composed of equivalent silica material. In one aspect, a $CO_2$ laser may be used to heat the two silica components together to form a single fused end section 29 with an energy emitting face 11A. When the silica or other material of the inner glass sleeve 13 is heated by the laser, it melts together with the fiber core 5 material, forming a curved (convex as shown) semi-spherical distal end profile, as shown in FIG. 3B. Other distal end profiles may optionally be formed by modifying the fusing process or by post-fusing shaping, using techniques known in the art. Shapes may include but are not limited to generally flat faced, with or without a radiused edge, convex and concave.

In one aspect, the fused end tip section 29 also effectively blocks the distal end of the air gap 31, creating an enclosed air cavity. This enclosed air cavity 31 acts as a cladding by containing light within core 5 and directing light energy in a forward manner. The cladding of a conventional fiber normally extends distally to just proximal to or flush with the energy emitting fiber core face 11. The cladding prevents emitted laser energy from exiting the side wall of the fiber core as the laser beam travels through the fiber, but the distal end section of the fiber where the energy is emitted, is often subject to localized heating during use. This heat build-up at the distal end section of a conventional fiber may reach temperatures high enough to melt or otherwise damage the fragile cladding layer. Once the cladding has been damaged, laser energy will escape radially through the side wall of the fiber core 5, causing increased localized heating with peak temperatures that may be high enough to further damage the distal end of the fiber.

In one exemplary aspect, the air gap 31 of the fiber assembly disclosed herein helps to reduce localized heat build-up and prevent thermal damage to the working end of the device 1. Since air has a lower refractive index than silica, air gap 31 functions as cladding to prevent laser energy from escaping the core. By removing the cladding 9, the possibility of burn back of the cladding is eliminated. The fused end tip section 29 ensures that blood will not contact the bare side walls of the fiber core 5. With conventional fibers, when the cladding burns back, blood in contact with the side wall of the bare fiber may carbonize and cause additional laser energy loss through the side wall. Continued energy loss through the side walls of the fiber causes the fiber to weaken and eventually break. The assembly 1 with air gap 31 eliminates problems due to cladding burn back and ensures that any errant laser energy that does escape through the core 5 will be reflected back into the core 5 by the presence of air gap 31, due to the air index of refraction. Thus, the air gap 31 serves as a "thermal-proof" waveguide to maintain the laser light within the core 5 as it travels through the unclad portion of the fiber 3 by ensuring that the energy travels in a forward direction and does not escape radially through the core side wall. The energy beam exits from the fused distal end section 29 through emitting face 11A of the fiber in a forward direction only.

FIG. 4 is an enlarged partial longitudinal plan view of the distal end section of the optical fiber with spacer assembly 1 after the optional outer protective sleeve 19 has been assembled over the inner glass sleeve 13/fiber 3 subassembly of FIG. 3. Prior to assembling the sleeve 19 with the inner glass sleeve 13/fiber 3 assembly, the proximal end 17 of the inner glass sleeve 13 is sealed against the cladding 10. Sealant 35 is applied to the gap between the leading edge 12 of the jacket 9 and the proximal edge 17 of the inner glass sleeve 13. A curable silicone-based liquid adhesive is applied to the annular gap using a small mandrel or other known application process. In one aspect, the liquid sealant may have a refraction index equivalent to the cladding 10. The sealant 35 applied to the gap is sufficient to completely seal the edge 17 of the inner glass sleeve 13 against the leading edge 30 of cladding 10 as well as to fill the space created by the inwardly tapered surface 32. Sealant 35 fills any gaps, cracks or other damage that may have occurred to the cladding 10 during the manufacturing process. The adhesive qualities of sealant 35 provide added strength to the device by increasing the bond strength between the fiber and inner glass sleeve 13. Thus, sealant 35 acts as a supplemental cladding by preventing any laser energy from escaping through the cladding 10 in this area. In one aspect, the amount of sealant 35 applied may create an outer diameter that is less than or equal to that of the inner glass sleeve 13 and protective jacket layer 9 of the fiber 3.

Outer protective sleeve 19 is then aligned over the inner glass sleeve/fiber subassembly so that the distal end 21 of sleeve 19 is positioned a distance distal to the emitting face 11A of fused end tip section 29. This distance may be equal to or greater than zero, such as 0.003 inches-0.008 inches or greater. In one aspect the sleeve 19 is positioned approximately 0.0065" from the distal end of the fused end tip 29. Adhesive may be applied to ensure that the outer protective sleeve 19 is retained in the desired position during assembly. Specifically, adhesive 39 may be applied to the annular space between fiber jacket 9 and the inner wall of outer protective sleeve 19. Adhesive 39 may also be applied to the proximal section of the annular space between the inner glass sleeve 13 and the outer sleeve 19. As shown in FIGS. 4 and 5, adhesive 39 extends from the distal edge of air gap 37 distally to adhesive termination point 40. A ring of adhesive 39 may also be applied to the proximal end of the outer protective sleeve 19. This ring not only provides enhanced fixation of the sleeve 19 to the fiber 3, but also provides a tapered outer profile to prevent the vein from catching on sleeve 19 as the device is withdrawn from the vessel.

Optionally, the proximal section of the outer protective sleeve 19 may be crimped at crimp area 33 to enhance the attachment strength between the sleeve 19 and the jacketed fiber 3. In one embodiment, the crimping process may force the wall of the outer protective sleeve 19 to be pressed into the adhesive layer 39, as shown by indentions 38 in FIG. 5A.

FIG. 5A illustrates an enlarged longitudinal cross-sectional view of the assembled distal end segment of the optical fiber with spacer assembly 1 disclosed herein. FIG. 5B-5E are axial cross-sections of the distal section of FIG. 5A taken along lines A-A, B-B, C-C and D-D, respectively. Referring to FIG. 5B, fiber 3 with its fiber core 5, cladding 10 and outer jacket 9 is coaxially surrounded by adhesive layer 39, which ensures a secure attachment to outer protective sleeve 19. Referring next to FIG. 5C, fiber core 5 and cladding 10 are coaxially surrounded by sealant 35. As with FIG. 5B, the outer protective sleeve 19 coaxially surrounds the subassembly, but the adhesive ring 39 has been replaced with air gap 37. Air gap 37 is optional and is based on the thickness of sealant 35 applied to the cladding 10 as well as the amount the sealant will shrink after drying. FIG. 5D illustrates the bare fiber core 5, reflective air gap 31, inner glass sleeve 13, outer air gap 41, and outer protective sleeve 19. FIG. 5E depicts the fused distal end section 29, comprised of the bare fiber core 5 fused together with the inner glass sleeve 13 as previously described and outer air gap 41 coaxially surrounded by the outer protective sleeve 19.

When laser energy travels down the fiber core 5, as it passes through Section A-A, the laser energy is directed in a forward direction by the cladding 10 and protective jacket 9. As the wave reaches Section B-B, the cladding 10 and sealant 35 ensure a continued forward travel of the energy. The silicone sealant provides additional protection by preventing laser energy from passing through any cracks or openings in the cladding inadvertently created during the manufacturing process. As the laser energy passes through Section C-C, any errant laser energy passing through and out of the side wall of core 5 due to the absence of cladding 10 will be reflected back into the core 5 by air gap 31 due to its lower index of refraction. Once the laser energy reaches Section D-D, the laser beam will pass through the fused distal end section 29 and be directed in a forward direction through energy emitting face 11A.

FIG. 6A through 6C illustrate the laser fiber 3 with energy emitting faces having several different surface areas and demonstrating the relationship between an increased surface area of the emitting face of the fiber and the average power density reduction. FIG. 6A is a partial plan view of the distal section of a conventional 600 micron fiber having a core 5 of diameter D1 with cladding 10 extending to the distal energy emitting face 11. Rays 71 depict the boundaries of the energy emission zone with a maximum propagation angle θ of energy emitted from the core 5. Angle θ is based on the numerical aperture of the fiber and the specific materials (core and cladding) being used. In one exemplary aspect, given a numerical aperture of 0.37, the propagation angle θ may be 16 degrees in water or blood, resulting in laser energy being distributed and emitted across the entire face 11 of the fiber, defined by diameter E1. In FIG. 6A, D1 is equal to energy emitting face 11 diameter E1. The average density of the laser energy at the emitting face 11 is based on the surface area of the face 11. For example, a 600 micron fiber has a surface area of about 0.0028 cm2, as shown in Table 1 below. At a power setting of 14 Watts, laser energy is emitted through the energy emitting face 11 at an average power density of 5 KWatts/cm2.

Table 1 below illustrates the reduction in power density at the distal end of the fiber as the effective diameter (E) of the energy emitting face 11A is increased. The fusion length (L) is listed in microns. The diameter of the effective emitting face E is recorded in microns. The surface area of the emitting face 11A is recorded in cm2. Due to the arcuate surface profile of the fused distal end section 29, the surface area data in Table 1, which is calculated using the area of a circle across a flat horizontal plane, represents the minimum surface area of energy emitting face 11A because it does not account for the additional surface area due to the convex profile of 11A. Average power density at the energy emitting face 11A is recorded in KWatts/cm2 and is based on an average power delivery of 14 Watts, the level commonly used for endovenous laser procedures, divided by the surface area of the emitting face. The recorded percent reduction in power density is relative to that of a conventional 600 micron fiber depicted in FIG. 6A, and is calculated as 100—(average power density/5.0).

TABLE 1

Power Density Reduction Table
For 600 Micron Fiber Core

| Fusion Length (L) (microns) | Effective Diameter of energy emitting face (E) (microns) | Surface area of emitting face (cm²) | Average Power density (KWatts/cm²) | Reduction in average power density |
|---|---|---|---|---|
| 0 | 600 | 0.0028 | 5.0 | 0% |
| 227 | 720 | 0.0041 | 3.4 | 31% |
| 265 | 740 | 0.0043 | 3.3 | 33% |
| 303 | 760 | 0.0045 | 3.1 | 38% |
| 341 | 780 | 0.0048 | 2.9 | 41% |
| 416 | 820 | 0.0053 | 2.7 | 47% |
| 492 | 860 | 0.0058 | 2.4 | 51% |
| 530 | 880 | 0.0016 | 2.3 | 54% |
| 606 | 920 | 0.0056 | 2.1 | 58% |
| 681 | 960 | 0.0072 | 1.9 | 61% |
| 719 | 980 | 0.0075 | 1.9 | 63% |
| 795 | 1020 | 0.0082 | 1.7 | 65% |
| 833 | 1040 | 0.0085 | 1.6 | 67% |
| 908 | 1080 | 0.0092 | 1.5 | 69% |
| 984 | 1120 | 0.0099 | 1.4 | 71% |
| 1022 | 1140 | 0.0102 | 1.4 | 72% |
| 1098 | 1180 | 0.0109 | 1.3 | 74% |
| 1135 | 1200 | 0.0113 | 1.2 | 75% |
| 1211 | 1240 | 0.0121 | 1.2 | 77% |
| 1249 | 1260 | 0.0125 | 1.1 | 77% |
| 1325 | 1300 | 0.0133 | 1.1 | 79% |
| 1400 | 1340 | 0.0141 | 1.0 | 80% |
| 1476 | 1380 | 0.0150 | 0.9 | 81% |
| 1514 | 1400 | 0.0154 | 0.9 | 82% |
| 1590 | 1440 | 0.0163 | 0.9 | 83% |
| 1627 | 1460 | 0.0167 | 0.8 | 83% |
| 1703 | 1500 | 0.0177 | 0.8 | 84% |

FIG. 6B is a plan view of the distal section of inner glass sleeve 13 and fiber 3 subassembly after the inner sleeve 13 and fiber 3 have been fused to form tip 29 using a laser fusion process. This figure illustrates the increase in the emitting face 11A surface area. In this aspect, the fiber core 5 is 600 microns with a diameter D1, equal to the conventional fiber core diameter D1 described in FIG. 6A. The maximum propagation angle θ emitted from the fused distal end 29 remains 16 degrees due to the core's numerical aperture of 0.37. As described above, the laser process fuses the inner glass sleeve 13 and the fiber core 5 creating a fusion length L1 that extends from the fused fiber tip section 29 of the fiber 3 to the distal end of the air gap cavity 31. The fusion length L1 increases the effective surface area of the emitting face 11A, as indicated by effective diameter E2 of the emitting face 11A, which is larger than the fiber emitting face 11 diameter of E1 of FIG. 6A. As an example, with reference to Table 1 above, a fusion length L1 of 341 microns will increase the effective diameter E2 of the emitting face 11A from 600 microns to 780 microns. The surface area will increase from 0.0028 cm2 to 0.0048 cm2. The average power density is reduced due to the increased surface area of the face 11A from 5.0 to 2.9 KWatts/cm2, representing a 40.5% reduction in power density as compared to the conventional fiber of FIG. 6A.

FIG. 6C illustrates a further increased fusion length L2. The fiber core 5 is 600 microns and has a diameter D1 equal to the core diameter of FIG. 6A. The laser fusion process creates a fusion between the inner glass sleeve 13 and the fiber core 5 with a fusion length L2 extending from the fused distal end section 29 to the distal end of the air gap cavity 31. As indicated by E3 of the emitting face 11A, the diameter of the energy emitting face 29 has increased relative to diameter E1 of FIG. 6A and E2 of FIG. 6B. This increase in diameter to E3 results in an increased surface area and reduced average power density at the emitting face 29. In one non-limiting example, with reference to Table 1, a fuse length L2 of 833 microns will increase the effective diameter of the emitting face 11A from 600 microns to 1040 microns. The surface area will increase from 0.0028 cm2 to 0.0085 cm2. The average power density is reduced relative to a standard 600 micron core fiber due to the increased surface area of the face 11A from 5.0 to 1.6 KWatts/cm2, representing a 66.7% reduction in average power density as compared to the conventional fiber illustrated in FIG. 6A.

Thus in one important aspect, by increasing the fuse length L between the fiber core 5 and silica cannula 13, an increase surface area of the fused energy-emitting face 11A is realized. The increased surface area of the fused emitting face 11A results in a substantial reduction in average power density at the emitting face 11A of the device without compromising the total amount of energy delivered to the vessel. As an example, by doubling the effective diameter of the energy emitting face 11A from 600 microns to 1200 microns, a 75% reduction in average power density can be realized.

Conventional fibers can often reach very high temperatures sometimes exceeding several thousand degrees at the energy-emitting face where the energy density is the greatest. Fiber components such as the cladding may easily burn back when exposed to these high temperatures, resulting in exposure of bare fiber core. Thermal runaway may even cause the fiber core itself to overheat and burn back. Forward transmission of the energy is compromised as laser energy escapes radially from the bare core. The errant laser energy often causes thermal runaway with extreme temperatures causing further erosion of the cladding and distal end segment of the fiber. With the configurations disclosed herein, the reduced average power density at the distal end of the fiber resulting from an increased surface area of the emitting face reduces peak temperatures and reduces the possibility of thermal run-away and device damage, without a decrease in the total amount of energy delivered during the treatment session. The reduced average power density also reduces the possibility of vessel perforations caused by extreme temperatures, leading to less bruising, post-operative pain and other clinical complications.

Figure 7:
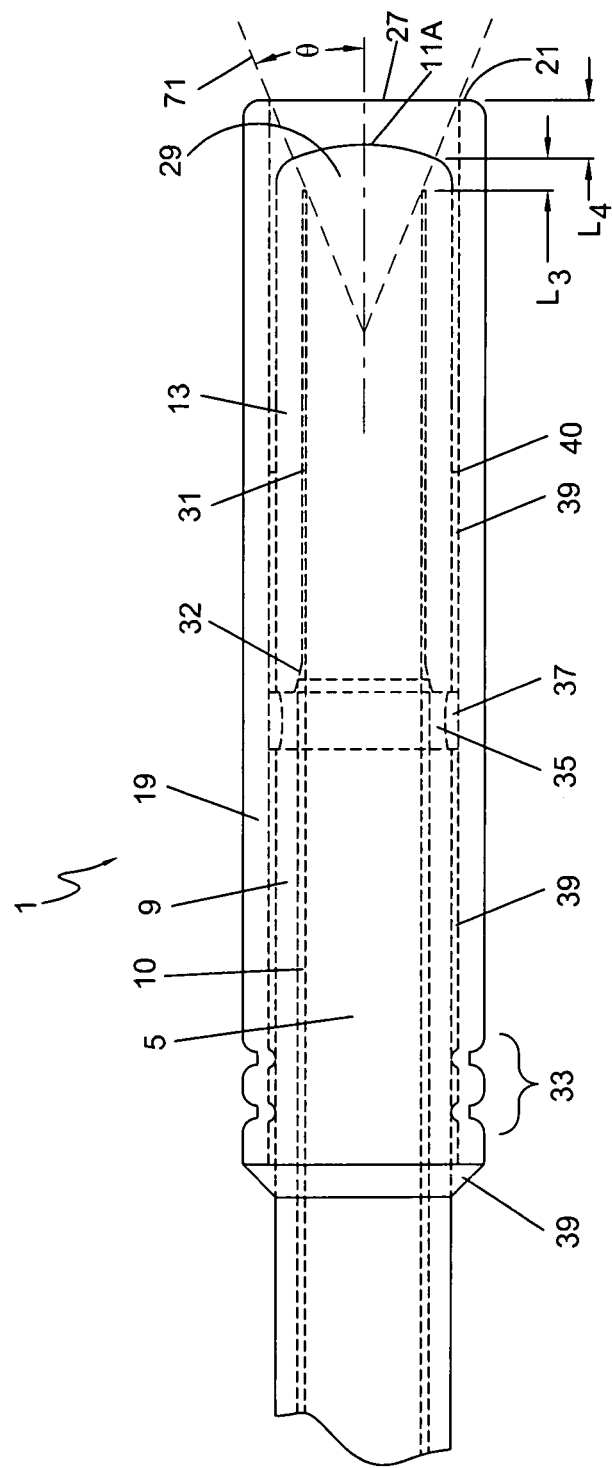
FIG. 7 is a partial plan view of the distal section of the optical fiber with spacer assembly illustrating the maximum propagation angle exiting from the outer protective sleeve lumen.

FIG. 7 is an enlarged partial plan view of the distal section of the device of the fiber with spacer assembly 1. The outer protective sleeve 19 is assembled as previously described with adhesive 39 and crimp area 33, ensuring attachment to the fiber 3/inner glass sleeve 13 assembly. Laser energy is emitted from the distal end of the fiber with a maximum propagation angle θ of the energy emission zone is defined by boundary rays 71. Laser energy passes through fused end section 29, is emitted out of emitting face 11A and into and through the lumen 27 of outer protective sleeve 19 at maximum angle θ. As illustrated in FIG. 7, outer boundary rays 71 do not contact the inner wall or leading edge 21 of outer protective sleeve 19.

The inner glass sleeve 13/fiber core 3 fusion length L3 determines length L4, defined as the length between the distal most edge of the fused end section 29 and the leading edge 21 of the outer protective sleeve 19. L4 represents the maximum extension of the outer protective sleeve 19 that can be used such that the laser energy exiting the emitting face 11A at the maximum angle θ does not contact the inner wall of outer protective sleeve 19. By controlling the dimensions of L3 and L4, laser energy following the maximum wave propagation angle θ will be directed into the blood vessel without directly hitting the distal end of the outer protective sleeve 19. Thus, overheating of the outer protective sleeve 19 caused by direct laser beam contact can be reduced with this invention, while still ensuring that the energy emitting face 11A is prevented from inadvertent contact with the vein wall.

The outer protective sleeve 19 may have a light-reflective coating such as gold. This coating may also be applied to a portion of the inner wall of the outer protective sleeve 19 along length L4. When a peripheral portion of the emission zone 71 beyond the emitting face 11A overlaps or otherwise contacts the distal portion of the inner wall of sleeve 19, the optional coating may increase reflection of laser energy into the vessel. Specifically any laser energy contacting the L4 portion of the sleeve 19 will be reflected off the sleeve and back into the treatment regions by the reflective qualities of the coating thereby avoiding emission energy loss and/or minimizing thermal build-up at the distal end of the device.

Referring now to FIG. 8A and FIG. 8B, an alternative embodiment of the fiber with spacer device 201 is illustrated. FIG. 8A is a partial longitudinal cross-sectional view of the distal segment of element 201. FIG. 8B shows an end view of the embodiment in FIG. 8A illustrated from the distal end of the device. The components in assembly 201 are of a smaller size and diameter compared to optical fiber with spacer assembly 1 of FIG. 5 to allow for direct advancement through the treatment vessel without the use of a treatment sheath or other tracking accessory. Fiber with spacer element 201 includes fiber 203, inner glass sleeve 213 and outer protective sleeve 219. As with previous embodiments, the fiber 203 with protective jacket layer 209 and cladding 210 extends partially through the outer protective sleeve 219. The protective jacket layer 209 terminates at distal end 212, adjoining air gap 237. The cladding 210 terminates just inside the inner glass sleeve 213 at the internal taper 232. Inner glass sleeve 213 coaxially surrounds fiber core 205 between which a constant-width annular air gap 231 is formed. The fiber core 205 further extends distally terminating at fused distal end section 229 in emitting face 11A. Coaxially positioned in surrounding relationship with the fiber/inner glass sleeve subassembly is the outer protective sleeve 219. Outer protective sleeve 219 extends distally beyond fused emitting face 11A terminating in leading edge 221.

In one example, the fiber core 205 is comprised of pure silica with a numerical aperture of 0.37 and may have a diameter of 500 microns or less, such as 400 microns. Corresponding outer diameter dimensions of other elements include the cladding 210 at 430 microns and outer jacket layer 209 at 620 microns, both of which extend distally into the outer protective sleeve 219. Outer jacket 209 terminates at point 212 and the cladding 210 terminates within the inner glass sleeve 213 just distal of the inner glass sleeve tapered wall section 232. In one exemplary aspect, inner glass sleeve 213 may have an outer diameter of 0.043 inches. Inner glass sleeve 312 may have an internal through lumen of approximately 0.0165 inches in diameter tapering outwardly to a flared diameter of 0.020 inches at proximal edge 232, an outer diameter of 0.033 inches and a length of 0.238 inches. The outer protective sleeve 219 has an internal through lumen 227 with a diameter of about 0.035 inches. With these dimensions, the annular air gap 231 is approximately 0.0001 inches in width, and as previously described, is closed at the proximal end by cladding 210 and silicone sealant ring 235 and by the fused inner glass sleeve/fiber tip 229 at the distal end.

The distal end view of the device, shown in FIG. 8B, illustrates the fused distal end section 229 with energy emitting face 11A coaxially surrounded by the outer protective sleeve 219. A small air gap 241 exists between fused end section 229 and sleeve 219. Shown with hidden lines is the air gap 231 which coaxially surrounds the fiber core 205 and the outer boundary of the energy emitting face 11A. The expanded distal end 226 of sleeve 219 is illustrated by apex 243.

Figure 10A:
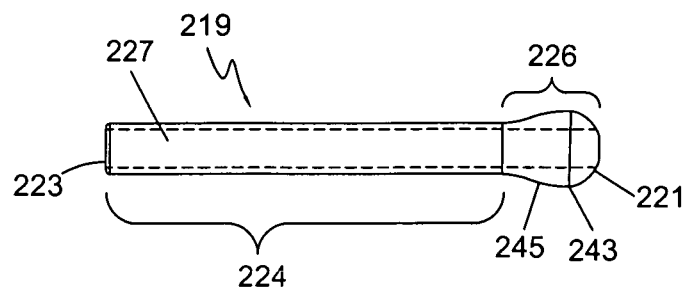
FIG. 10A through 10D illustrate various embodiments of the outer protective sleeve.

Referring to FIGS. 8A, 8B and 10A, outer protective sleeve 219 is comprised of a proximal edge 223, a cylindrical main body 224, an outwardly bulging distal body/portion 226 extending from the main body, with a through lumen 227 of constant diameter of approximately 0.035 inches extending from edge 223 to tip 221. As shown in FIG. 8A, the bulging distal body 226 has a bulb-like profile or shape. The main body 224 may be approximately 0.360 inches in length. The outwardly bulging body 226 extends distally from the main body 224 for approximately 0.040 inches. Outwardly bulging distal body 226 includes a radially outwardly tapering section 245, which in one aspect may have a taper angle of 170 degrees relative to the longitudinal axis of fiber core 205. Tapering section 245 extends outwardly to a maximum diameter at apex 243, which in the instant embodiment may have an outer diameter of 0.054 inches. Thus, at the apex 243, the wall thickness of sleeve 19 may be approximately 0.0095 inches, which is approximately twice the thickness of the main body wall which is approximately 0.0055 inches. The outwardly bulging distal body 226 tapers radially inward from apex 243 to distal end 221, which may be radiused to eliminate any sharp edges and provide a smooth leading tip.

The increased wall thickness and surface area of the bulging distal body 226 relative to the main body 224 provides enhanced trackability when inserting and advancing the fiber 203 to the treatment location. The distal end segment 226 acts as an atraumatic leading tip, which will not perforate the vessel wall if contact is made between outer protective sleeve 219 and the vessel wall during advancement through the vein. The additional surface area and material at the distal end of the device also provides enhanced trackability and pushability through the vessel. The additional material at the distal body 226 of sleeve 219 adds structural strength to the distal end of the device making it less susceptible to thermal damage by reducing peak temperatures at the distal end of the device.

In one aspect, use of a smaller fiber such as a 400 micron fiber provides a sufficiently flexible fiber shaft to allow insertion and advancement through the vein without having to use a guidewire or treatment sheath. Due to the small diameter, the fiber with spacer assembly 201 may be inserted directly through a micro-access set into the vein, thereby eliminating several procedural steps as will be described in more detail below. A 400 micron fiber is also capable of delivering sufficient energy to cause vessel occlusion. It may be desirable to use a fiber with a diameter of 430 microns to provide additional fiber core diameter at the proximal end where the fiber connects to a laser source. The larger diameter core will allow for slight misalignment of the fiber core to laser source without compromising energy transmission or damaging the laser generator.

Although the fiber diameter is smaller than the previously disclosed 600 micron fiber, the creation of a fused distal end section 229 with its fusion length L will also effect the reduction in power density at the emitting face 11A. Table 2 below lists the average reduction in power density based on increasing fusion lengths.

TABLE 2

Power Density Reduction Table
For a 400 Micron Fiber Core

| Fusion Length (L) (microns) | Effective Diameter of energy emitting face (E) (microns) | Surface area of emitting face (cm$^2$) | Average Power density (KWatts/cm$^2$) | Reduction in average power density |
|---|---|---|---|---|
| 0 | 400 | 0.0013 | 11.1 | 0% |
| 200 | 502 | 0.0020 | 7.1 | 36% |
| 300 | 553 | 0.0024 | 5.8 | 48% |
| 400 | 604 | 0.0029 | 4.9 | 56% |
| 500 | 655 | 0.0034 | 4.2 | 63% |
| 600 | 705 | 0.0039 | 3.6 | 68% |
| 700 | 756 | 0.0045 | 3.1 | 72% |
| 800 | 807 | 0.0051 | 2.7 | 75% |
| 900 | 858 | 0.0058 | 2.4 | 78% |

FIG. 9A is a partial plan view of the fiber with spacer assembly illustrating a fiber 3 and proximal section of the outer protective sleeve 19. Fiber 3 is comprised of a core 5, a cladding layer 10, coaxially surrounded by protective jacket 9, and attached to outer protective sleeve 19 as previously disclosed. As illustrated in FIG. 9A, the device may include visual markings/markers 18 on the outer jacket 9 of fiber 3. Markings 18 are used by the physician to provide a visual indication of insertion depth, tip position and speed at which the device is withdrawn through the vessel during delivery of laser energy. The markings 18 may be numbered to provide the physician with an indication as to distance from the protective sleeve 19 and/or the emitting face 11A of the fiber to the access site during pullback. The markings 18 may be positioned around the entire circumference of the fiber shaft or may cover only a portion of the shaft circumference.

As the device is pulled back, the markings appear at the skin surface through the access site and provide the physician with a visual indication of pullback speed. In one example, given a 10 watt power setting, the rate at which the device is retracted is approximately 5-8 seconds per cm. In one exemplary aspect, markings 18 may be approximately 1 mm in width and be aligned at 1 cm increments. Optionally the distal most set of markings 59 may be uniquely configured to visually alert the physician that the distal end of the fiber with the outer protective sleeve 19 is near the access site, indicating that the procedure is complete.

FIG. 9B illustrates yet another embodiment of the fiber with spacer assembly 1. In this embodiment, a metallic reinforcement element 20 coaxially surrounds fiber 3 and extends from the proximal end of the fiber (not shown) to the distal end section adjacent to or overlapping with the optional outer protective sleeve 19. Metallic reinforcement element 20 may be comprised of metallic strands 69 arranged in an overlapping braided pattern, as shown in FIG. 9B, or other patterns such as spiral or longitudinal or horizontally arranged strands. In one exemplary aspect, strands 69 are embedded within a polymer layer 79. Layer 79 may be an extruded urethane, Teflon shrink tubing or other plastic material known in the art. The outer surface of metallic reinforcement element 20 may be hydrophilically coated to reduce friction during advancement and retraction of the fiber. In one aspect, metallic strands 69 may optionally overlap with the proximal section of outer protective sleeve 219. Overlapping metallic strands 40 may be sandwiched between the inner wall of outer protective sleeve 219 and the fiber jacket 9. The polymer layer 79 may optionally be removed from the metallic strands 40 and the strands welded to the outer protective sleeve 19.

Metallic reinforcement element 20 provides several advantageous functions. Visibility of the entire fiber shaft 3 under ultrasound imaging is enhanced due to the echogenicity of the metallic strands 69. Enhanced visibility of the fiber shaft provides the physician with an ultrasonically visible target when injecting tumescent fluid into the anatomical perivenous sheath along the length of the vein prior to the delivery of laser energy, as is described in more detail below. Enhanced visibility of the fiber shaft provides the physician with a visual target for positioning the tumescent injection needle accurately between the outer vein wall and the perivenous sheath without entering the vein lumen. If the needle tip inadvertently enters the vessel lumen and comes into contact with the fiber, the presence of the metallic reinforcement element 20 provides an added level of protection to the fiber shaft to prevent damage to the cladding 10 and core 5 from the sharp needle tip. Typically, tumescent fluid is injected all along the vessel being treated using a small gauge needle. The needle tip may inadvertently contact the fiber shaft during this step, causing damage. The additional reinforcement layer prevents the needle from damaging the protective jacket 9 and the cladding 9, thereby preventing the possibility of laser energy escaping radially from the fiber core 5 through the compromised jacket or cladding. In another aspect, the optional weld between the outer protective sleeve 19 and the bare metallic strands 40 increases the overall structural integrity of the distal end segment by providing a supplemental attachment region.

Figure 10B:
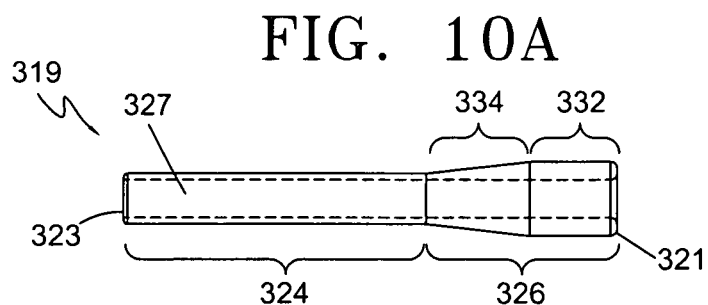
Figure 10C:
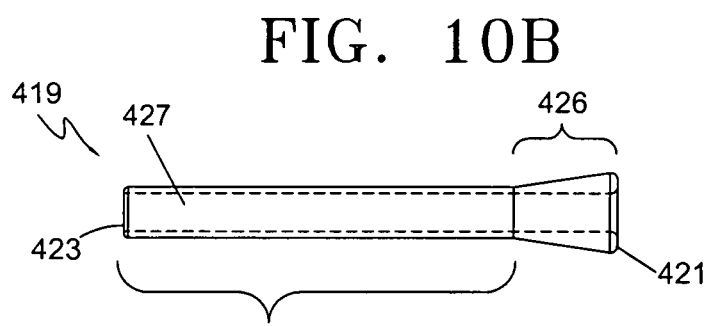
Figure 10D:
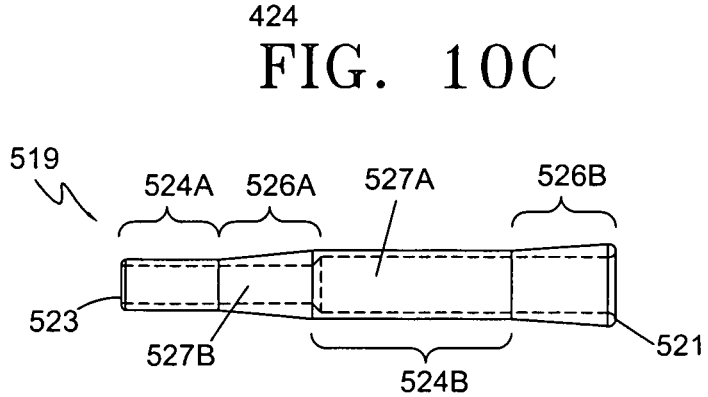

Other outer protective sleeve 19 configurations are illustrated in FIGS. 10B through 10D. The sleeve 319 profile may include a bulging distal end segment/portion 326 as shown in FIG. 10B. In this embodiment, distal end segment 326 includes an outwardly tapering section (conical shape portion) 334 which transitions to cylindrical segment 332, which has a constant diameter, before terminating in radiused end 321. FIG. 10C illustrates a plan view of outer protective sleeve 419 showing a bulging distal end segment/portion 426 that extends from main body 424 radially outward at a constant angle (conical shape portion) before terminating in radiused end tip 421. FIG. 10D illustrates yet another embodiment of sleeve 519. The sleeve includes a cylindrical portion 524A and an outwardly bulging portion 526A, 524B and 526B. Conical shape portion 526A extends distally from the cylindrical portion 524A with increasing diameter. Cylindrical portion 524B extends from conical shape portion 526A and has a larger diameter than that of cylindrical portion 524A. Second conical shape portion 526B extends from cylindrical portion 524B and has a radiused end (distal tip) 521. A through lumen 527 extends from distal tip 521 and includes an internal transition from a larger diameter section 527A to a smaller diameter section 527B before terminating at proximal end 523. This embodiment may be used to accommodate a larger inner diameter inner glass sleeve relative to the fiber outer diameter. The multiple tapered segments of FIG. 10D also provide a more gradual taper transition across the entire longitudinal length of the outer protective sleeve 519, which allows for both enhanced tracking of the device to the target treatment location and enhanced retracting of the device through the vein during laser delivery.

FIGS. 11A and 11B depict the fiber assembly 601 in which the inner glass sleeve 613 is illustrated as an additional embodiment. The embodiment of FIG. 11 is similar to that of FIGS. 2 and 3, except that the sleeve 613 has a closed distal end 627 prior to being fused with the fiber core 5. Fiber 3 includes a core 5, cladding 10, and outer protective jacket 9 with an energy emitting face 11. Cladding 10 has been partially stripped back to edge 30, and protective jacket 9 has also been partially stripped back to edge 12, as previously described. As shown in FIG. 11A, inner glass sleeve 613 includes a proximal edge 617, and leading end wall 627 and a cavity 675 extending proximally from wall 627 to edge 617. To assemble with the sleeve 613 with fiber 3, the front emitting face 11 of fiber 3 is inserted into and advanced through cavity 675 until it abuts up against wall 627. A $CO2$ laser is then used to heat the two silica components 11 and 627 together to form a single fused end tip (not shown) with a radiused surface profile so that an enlarged emitting face is created. Similar to the embodiment as shown in FIGS. 2 and 3, the constant-width air gap 631 acts as a cladding layer to reduce light transmission loss. The fused tip reduces the thermal load (average power density) at the distal tip 627 and prevents erosion of the tip section.

Figure 12:
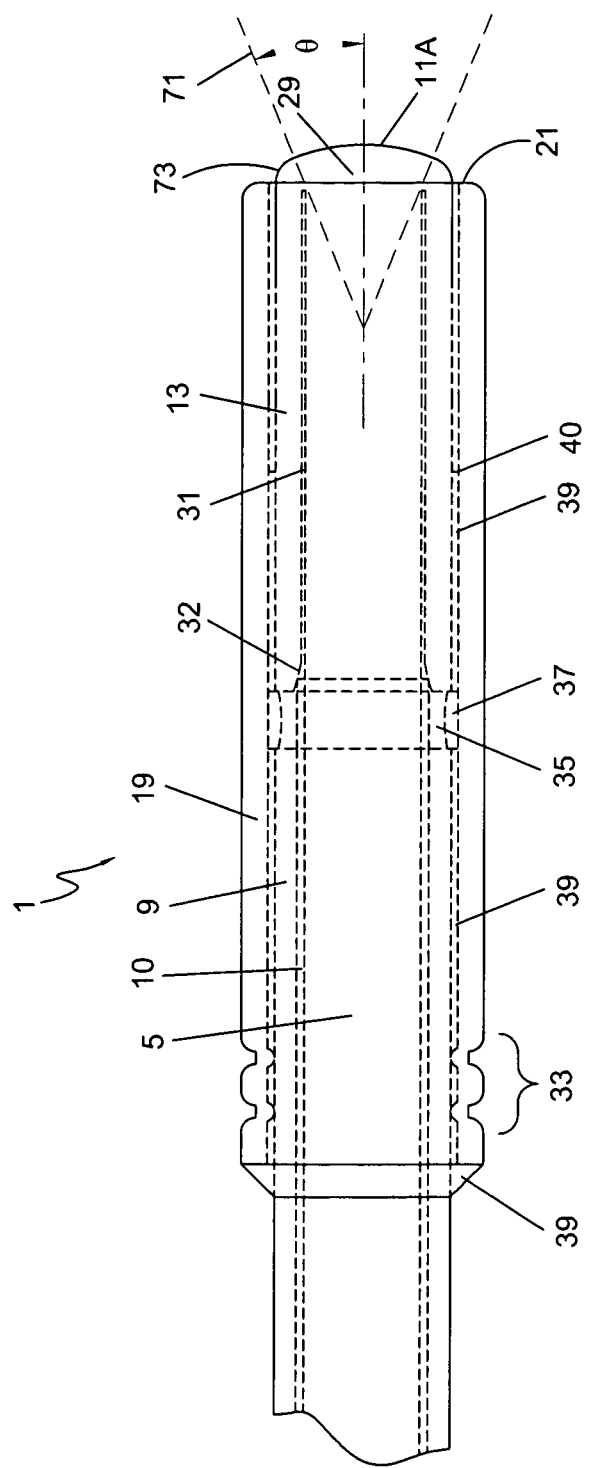
FIG. 12 is a partial plan view of the distal section of the optical fiber with spacer assembly depicting an alternative embodiment of the outer protective sleeve.

FIG. 12 is an enlarged partial plan view of the distal section of the device of the fiber with spacer assembly 1 with an outer protective sleeve 19 whose distal end 21 terminates proximally of the energy emitting face 11A. The outer protective sleeve 19 may be aligned over the inner glass sleeve 13 so that fused end section 29 of the device extends distally beyond the leading edge 21 of outer protective sleeve 19. In one aspect, the leading edge 21 of outer protective sleeve 19 may be between 0.5-5.0 mm proximal to emitting face 11A. The protective spacer 19 may be of the same length as previously described or may be shorter in overall length. Other than the recessed alignment relative to the emitting end 29, the outer protective sleeve 19 is assembled as previously described with adhesive 39 and crimp area 33. The outer boundaries of the energy emitting face 11A are defined by maximum propagation angle $\theta$ of the energy emission zone 71. As indicated by rays 71, the energy emitting face 11A is protected from contact with the vessel wall by the leading radiused surface 73 of inner sleeve 13. The outer protective sleeve 19 in this embodiment ensures that laser energy emitting from emitting face 11A will not come into contact or reflect off the distal section of the outer protective sleeve 19, regardless of the maximum propagation angle $\theta$ of the energy emission zone. Thus, the outer protective sleeve 19 provides increased structural integrity and strength to the distal section of the device while minimizing overheating of the outer protective sleeve 19 caused by peripheral laser beam contact.

Methods of using the optical fiber with spacer assembly for endovenous treatment of varicose veins and other vascular disorders will now be described with reference to FIGS. 13 and 14. FIG. 14 illustrates the procedural steps associated with performing endovenous treatment using the optical fiber with spacer assembly 1. To begin the procedure, the target vein is accessed using a standard Seldinger technique well known in the art. Under ultrasonic guidance, a small gauge needle is used to puncture the skin and access the vein (100). A 0.018 inches guidewire is advanced into the vein through the lumen of the needle. The needle is then removed leaving the guidewire in place (102).

A micropuncture sheath/dilator assembly is then introduced into the vein over the guidewire (104). A micropuncture sheath dilator set, also referred to as an introducer set, is a commonly used medical kit, for accessing a vessel through a percutaneous puncture. The micropuncture sheath set includes a short sheath with internal dilator, typically 5-10 cm in length. This length is sufficient to provide a pathway through the skin and overlying tissue into the vessel, but not long enough to reach distal treatment sites. Once the vein has been access using the micropuncture sheath/dilator set, the dilator and 0.018 inches guidewire are removed (106), leaving only the micropuncture introducer sheath in place within the vein (107). A 0.035 inches guidewire is then introduced through the introducer sheath into the vein. The guidewire is advanced through the vein until its tip is positioned near the sapheno-femoral junction or other starting location within the vein (108).

After removing the micropuncture sheath (110), a treatment sheath/dilator set is advanced over the 0.035 inches guidewire until its tip is positioned near the sapheno-femoral junction or other reflux point (112). Unlike the micropuncture introducer sheath, the treatment sheath is of sufficient length to reach the location within the vessel where the laser treatment will begin, typically the sapheno-femoral junction. Typical treatment sheath lengths are 45 and 65 cm. Once the treatment sheath/dilator set is correctly positioned within the vessel, the dilator component and guidewire are removed from the treatment sheath (114, 116).

The optical fiber with spacer assembly 1 is then inserted into the treatment sheath lumen and advanced until the fiber assembly distal end is flush with the distal tip of the treatment sheath (118). A treatment sheath/dilator set as described in co-pending U.S. patent application Ser. No. 10/836,084, incorporated herein by reference, may be used to correctly position the protected fiber tip with spacer assembly 1 of the current invention within the vessel. The treatment sheath is retracted a set distance to expose the fiber tip (120), typically 1 to 2 cm. If the fiber assembly has a connector lock as described in U.S. Pat. No. 7,033,347, also incorporated herein by reference, the treatment sheath and fiber assembly are locked together to maintain the 1 to 2 cm fiber distal end exposure during pullback.

The physician may optionally administer tumescent anesthesia along the length of the vein (122). Tumescent fluid may be injected into the peri-venous anatomical sheath surrounding the vein and/or is injected into the tissue adjacent to the vein, in an amount sufficient to provide the desired anesthetic effect and to thermally insulate the treated vein from adjacent structures including nerves and skin. Once the vein has been sufficiently anesthetized, laser energy is applied to the interior of the diseased vein segment. A laser generator (not shown) is turned on and the laser light enters the optical fiber 3 from its proximal end. While the laser light is emitting laser light through the emitting face, the treatment sheath/fiber assembly is withdrawn through the vessel at a pre-determined rate, typically 2-3 millimeters per second (124). The laser energy travels along the laser fiber shaft through the energy-emitting face of the fiber and into the vein lumen, where the laser energy is absorbed by the blood present in the vessel and, in turn, is converted to thermal energy to substantially uniformly heat the vein wall along a 360 degree circumference, thus damaging the vein wall tissue, causing cell necrosis and ultimately causing collapse/occlusion of the vessel.

The optical fiber with spacer assembly 1 according to the invention has several advantages over methods of use of conventional bare-tipped fibers. The energy emitting face of the fiber assembly is protected from any inadvertent contact with the vessel wall during withdrawal of the device through the vessel during energy delivery. Numerous studies have demonstrated that contact between the energy emitting face of the fiber and the vein wall causes vessel perforations resulting in post-procedural bruising, pain and swelling. The inner glass sleeve and optional outer protective sleeve function to space the energy emitting fiber distal tip away from the vessel wall and to protect the emitting face within the outer protective sleeve recess, thus eliminating any possibility of contact between the fiber emitting face and the vessel and the resulting perforations, even when withdrawing through an extremely tortuous vessel.

The fiber with spacer assembly 1 of the current invention also is advantageous in controlling the direction and density of laser energy emitted from the emitting face of the fiber. The inner glass sleeve with annular air gap cavity ensures that the laser energy is contained in the fiber core and emitted in a forward direction only. Errant laser energy may compromise the structural integrity of the fiber tip by causing temperature spikes, localized heat build-up at the distal tip section and possible thermal run-away as described above. The inner glass sleeve and air gap cavity act to re-direct any errant laser energy back into the fiber core thus preventing reflected laser energy from being absorbed by the outer protective sleeve or other distal end elements.

In yet another aspect of the method of this invention, reduction in the average power density on the energy-emitting face of the fiber lowers the peak temperatures and thermal build-up at the distal end of the device while still delivering laser energy equivalent to a conventional bare fiber. As the fiber assembly is withdrawn through the vessel, clinically beneficial levels of laser energy are delivered to the vessel without heating up the distal end of the fiber assembly, greatly reducing the likelihood of thermal runaway. Thermal runaway creates extreme temperature variations that may result in incompletely treated vessel segments, perforation in the vein wall, carbonization tracks, and device failure.

Figure 13:
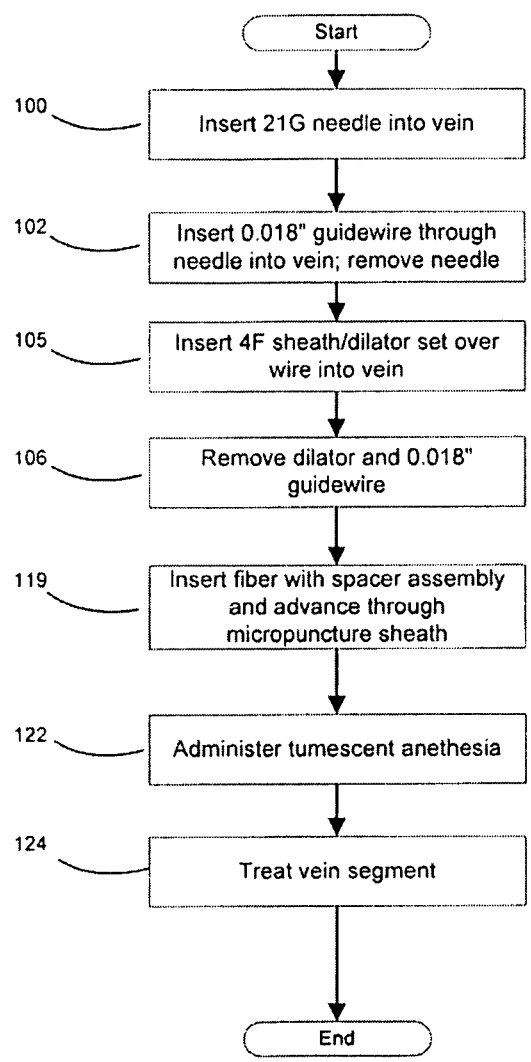
FIG. 13 is a flowchart depicting the method steps for performing endovenous laser treatment using the device of FIG. 5.
Figure 14:
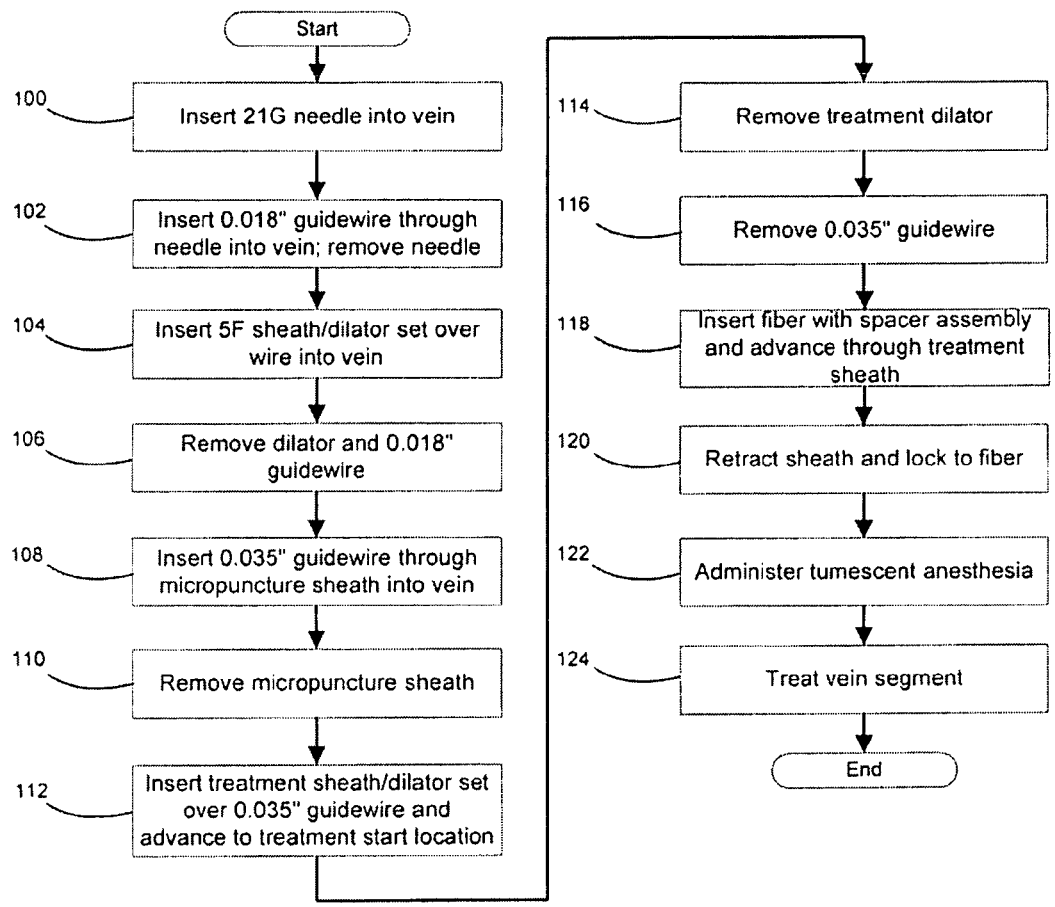
FIG. 14 is a flowchart depicting the method steps for performing endovenous laser treatment using the device of FIG. 8A.

FIG. 13 is a flowchart illustrating the procedural steps of the preferred method of endovenous treatment using the optical fiber with spacer assembly 201, which is depicted in FIGS. 8A and 8B. In this procedure, the use of a treatment sheath is not required due to the flexibility and trackability of the smaller diameter fiber device. As with the previously described method, the vein is accessed using a small needle and a 0.018 inch guidewire (100, 102). A micropuncture introducer sheath/dilator is then introduced into the vein over the guidewire (105) to dilate the insertion site. The dilator and guidewire are then removed (106), leaving the 4F sheath in place. Because the treatment sheath is eliminated with this method, the insertion site does not require dilation larger than the diameter of the 4F micropuncture sheath. Thus, the size of the micropuncture sheath/dilator assembly may be relatively small and the resulting access site puncture may be reduced relative to conventional methods. As is well-known in the art, smaller access sites are desirable as evidenced by the reduced occurrence of patient complications which may include hematoma, bleeding, pain, access site scarring and infection.

The 0.018 inch guidewire and dilator/sheath are removed from the patient, after which the optical fiber with spacer assembly is inserted directly into the vein through the 4F micropuncture sheath (119) without the aid of a treatment sheath. The fiber assembly is advanced forward through the vessel using the outwardly bulging distal tip of the outer protective sleeve 19 to facilitate advancement and tracking through tortuous vessels. The expanded distal end of the outer protective sleeve provides an atraumatic leading end, which will not catch or snag on the vessel wall as the fiber assembly is being advanced, but instead will glide along the vein wall. Because the fiber assembly is smaller and more flexible than larger diameter conventional fibers and can track easily through the vessel without a treatment sheath, numerous conventional procedural steps may be eliminated. For example, the step of inserting, advancing and positioning the 0.035 inches guidewire at the highest point of reflux within the vein is eliminated. The 0.035 inches guidewire is required in conventional methods in order to advance a treatment sheath/dilator set through the vessel. The steps of inserting a treatment sheath/dilator set, removing the dilator and removing the 0.035 inches guidewire are eliminated. Instead, the fiber assembly according to the present invention is inserted and advanced in the vessel without these procedure components. In addition, the steps of retracting the treatment sheath to expose the distal 1-2 cm of the fiber and locking the two components together prior to the delivery of laser energy is eliminated. In conventional procedures, misalignment of the fiber tip may result in thermal energy being transferred to the treatment sheath tip, resulting in potential damage to the treatment sheath and/or patient complications. With the improved and simplified method disclosed herein, the fiber assembly is positioned relative to the sapheno-femoral junction or other reflux point without having to align the fiber tip with a treatment sheath tip.

Laser energy is applied to the interior of the diseased vein segment as the fiber assembly is withdrawn, preferably at a rate of about 2-3 millimeter per second (124). The process of controlling the pullback speed through the vessel in conventional methods is typically controlled by the use of graduated markings on the treatment sheath. Since the treatment sheath is not present with the current method, the physician's pullback speed may be controlled either by markings positioned along the fiber shaft or by using an automated pullback mechanism, as is known in the art. The procedure for treating the varicose vein is considered to be complete when the desired length of the target vein has been exposed to laser energy.

The method of endovenous laser treatment disclosed herein has numerous advantages over prior art treatment devices and methods. The design of the distal end segment of the fiber assembly with its inner glass sleeve and optional outer protective sleeve provide the benefits previously described. In addition to these previously described benefits, the fiber with spacer assembly, with its smaller fiber size and atraumatic leading distal tip result in the elimination of multiple procedure steps required in conventional methods. Accessory components such as the 0.035 inch guidewire, treatment sheath and fiber/sheath locking connections are eliminated, thus reducing the overall cost of the device and procedure. Since the procedure has been simplified, the time associated with the eliminated steps is saved resulting in a faster, safer and more cost-effective procedure. The leading atraumatic distal tip not only provides a mechanism for easily tracking and advancing the fiber assembly in an atraumatic way through tortuous anatomy, but also facilitates the alignment of the fiber emitting face relative to the source of reflux, due to the enhanced ultrasonic visibility of the distal tip section.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein, which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the selected embodiments of the invention. Those skilled in the art may recognize other equivalents to the specific embodiments described herein which equivalents are intended to be encompassed by the claims attached hereto.

What is claimed is:

1. An endovascular laser treatment device for causing closure of a blood vessel comprising:
    an optical fiber adapted to be inserted into a blood vessel and having a core through which a laser light travels, the core having a proximal portion directly surrounded by a first cladding layer and a distal portion disposed distally of the proximal portion and directly surrounded by a second cladding layer that is different than the first cladding layer;
    an inner sleeve arranged around the distal portion of the core such that distal ends of the inner sleeve and the optical fiber core together form a single enlarged light emitting surface, wherein the inner sleeve is index matched with the core, the first cladding layer positioned proximally of the second cladding layer, the second cladding layer extending proximally from the enlarged light emitting face; and
    an outer sleeve arranged around the inner sleeve to position the light emitting surface away from an inner wall of the blood vessel.
2. The device according to claim 1, wherein the light emitting surface has a curved profile.
3. The device according to claim 1 wherein the outer sleeve has an outwardly bulging portion.
4. The device according to claim 3, wherein the outwardly bulging portion has a bulb-like profile.
5. The device according to claim 3, wherein the outwardly bulging portion has a conical shape portion whose diameter increases in the distal direction.
6. The device according to claim 3, wherein the outwardly bulging portion has:
    a conical shape portion whose diameter increases in the distal direction; and
    a cylindrical portion extending distally from the conical shape portion.
7. The device according to claim 3, wherein the outwardly bulging portion has:
    a first conical shape portion whose diameter increases in the distal direction;
    a cylindrical portion extending distally from the first conical shape portion; and
    a second conical shape portion extending distally from the cylindrical portion.
8. The device according to claim 1, wherein the distal end of the outer sleeve has a radiused profile to provide a smooth advancement through the blood vessel.
9. The device according to claim 1, wherein the light emitting surface is positioned a fixed distance proximally from the distal end of the outer sleeve.
10. The device according to claim 1, wherein the light emitting surface is positioned a fixed distance distally from the distal end of the outer sleeve.
11. The device according to claim 1, wherein the second cladding layer is an annular air cladding sleeve.
12. The device according to claim 11, wherein the annular air cladding has a closed distal end.
13. The device according to claim 11, wherein the annular air cladding has a closed distal end and a closed proximal end.
14. The device according to claim 11, wherein the annular air cladding has a constant width.
15. The device according to claim 1, wherein the core of the optical fiber is less than 600 microns in diameter.
16. The device according to claim 1, wherein the core of the optical fiber is less than 450 microns in diameter.
17. The device according to claim 1, wherein the distal ends of the inner sleeve and the core are fused to form the enlarged light emitting surface.
18. The device according to claim 17, wherein the distal ends of the inner sleeve and the core are heat fused.
19. The device according to claim 1, wherein:
    the inner sleeve has a closed distal end; and
    the closed distal end of the inner sleeve and the distal end of the core are heat fused to form the enlarged light emitting surface.
20. The device according to claim 1, wherein:
    the inner sleeve is a silica sleeve; and
    the distal ends of the silica sleeve and the core are fused to form the enlarged light emitting surface.
21. The device according to claim 1, wherein the outer sleeve is a metallic outer sleeve.
22. The device according to claim 21, wherein the metallic outer sleeve has a TiN coating.
23. The device according to claim 1, further comprising a plurality of spaced markers disposed along a wall of the optical fiber.
24. The device according to claim 1, further comprising a reinforcement element disposed along a wall of the optical fiber, the reinforcement element being ultrasonically visible.
25. The device according to claim 24, wherein the reinforcement element is a metallic element that extends around the optical fiber and along the wall of the optical fiber.
26. An endovascular laser treatment device for causing closure of a blood vessel comprising:
    an optical fiber adapted to be inserted into a vein and having a core through which a laser light travels, the core having an enlarged light emitting face at its distal end, the core having a proximal portion directly surrounded by a first cladding layer and a distal portion disposed distally of the proximal portion and directly surrounded by a second cladding layer that is different than the first cladding layer, the first cladding layer positioned proximally of the second cladding layer, the second cladding layer extending proximally from the enlarged light emitting face;

an inner sleeve arranged around the core and index matched with the core;

a spacer sleeve arranged around the distal portion of the core and around the entire longitudinal length of the inner sleeve to position the light emitting face away from an inner wall of the vessel.

27. The device according to claim 26, wherein:
the optical fiber has a silica cladding as the first cladding layer.

28. The device according to claim 27, wherein the spacer sleeve is a metallic sleeve.

29. The device according to claim 26, wherein the spacer sleeve is a metallic sleeve.

30. The device according to claim 26, wherein the light emitting face is positioned a fixed distance proximally from the distal end of the spacer sleeve.

31. The device according to claim 26, wherein the light emitting face is positioned a fixed distance distally from the distal end of the spacer sleeve.

32. The device according to claim 26, further comprising a plurality of spaced markers disposed along a wall of the optical fiber.

33. The device according to claim 26, further comprising a reinforcement element disposed along a wall of the optical fiber, the reinforcement element being ultrasonically visible.

34. An endovascular laser treatment device for causing closure of a varicose vein comprising:

an optical fiber adapted to be inserted into a vein and having a core through which a laser light travels, the core having a proximal portion directly surrounded by a first cladding layer and a distal portion disposed distally of the proximal portion and directly surrounded by a second cladding layer that is different than the first cladding layer;

a sleeve arranged around the distal portion of the core such that distal ends of the sleeve and the optical fiber core together form a single enlarged light emitting surface so as to lower the power density of emitted laser light, wherein the sleeve is index matched with the core, the first cladding layer positioned proximally of the second cladding layer, the second cladding layer extending proximally from the enlarged light emitting face.

35. The device according to claim 34, wherein the light emitting surface has a convex profile.

36. The device according to claim 34, further comprising an outer sleeve arranged around the sleeve to position the light emitting surface away from an inner wall of the varicose vein.

37. The device according to claim 36, wherein the outer sleeve is a metallic outer sleeve.

38. The device according to claim 36, wherein the light emitting surface is positioned a fixed distance proximally from the distal end of the outer sleeve.

39. The device according to claim 36, wherein the light emitting surface is positioned a fixed distance distally from the distal end of the outer sleeve.

40. The device according to claim 34, wherein the second cladding layer is an annular air cladding positioned between the core and the sleeve.

41. The device according to claim 34, wherein the distal ends of the sleeve and the core are fused to form the enlarged light emitting surface.

42. The device according to claim 34, wherein the distal ends of the sleeve and the core are heat fused to form the enlarged light emitting surface.

43. The device according to claim 34, wherein:
the sleeve has a closed distal end; and
the closed distal end of the sleeve and the distal end of the core are heat fused to form the enlarged light emitting surface.

44. The device according to claim 34, wherein:
the sleeve is a silica sleeve; and
the distal ends of the silica sleeve and the core are fused to form the enlarged light emitting surface.

45. The device according to claim 34, wherein:
the sleeve has substantially the same material as the core and is arranged to define an annular air gap between the sleeve and the core, as the second cladding layer; and
distal ends of the sleeve and the optical fiber core form a heat fused enlarged light emitting surface.

46. The device according to claim 34, wherein the light emitting surface has an increase of 30% to 73% in effective diameter E relative to the core diameter.

47. The device according to claim 45, wherein the light emitting surface has an increase of 30% to 73% in effective diameter E relative to the core diameter.

48. The device according to claim 47, wherein the light emitting surface has an increase of 47% to 67% in effective diameter E relative to the core diameter.

49. The device according to claim 45, wherein the light emitting surface is adapted to reduce average power density by 54% to 61%.

50. The device according to claim 47, wherein the light emitting surface is adapted to reduce average power density by 54% to 61%.

51. An endovascular laser treatment device for causing closure of a blood vessel comprising:

a single optical fiber adapted to be inserted into a vein and having a core through which a laser light travels, the core of the single optical fiber having an enlarged light emitting face at its distal end, the core having a proximal portion directly surrounded by a first cladding layer and a distal portion disposed distally of the proximal portion and directly surrounded by a second cladding layer that is different than the first cladding layer, the first cladding layer positioned proximally of the second cladding layer, the second cladding layer extending proximally from the enlarged light emitting face;

an inner sleeve arranged around the core and index matched with the core;

a spacer sleeve arranged around the inner sleeve to position the light emitting face away from an inner wall of the vessel.

52. The device according to claim 51, wherein the spacer sleeve is a metallic sleeve.

53. The device according to claim 51, wherein the light emitting face is positioned a fixed distance proximally from the distal end of the spacer sleeve.

54. The device according to claim 51, wherein the light emitting face is positioned a fixed distance distally from the distal end of the spacer sleeve.

* * * * *